(12) United States Patent
Altevogt et al.

(10) Patent No.: US 10,400,037 B2
(45) Date of Patent: Sep. 3, 2019

(54) BINDING MOLECULES, ESPECIALLY ANTIBODIES, BINDING TO L1CAM (CD171)

(71) Applicant: DEUTSCHES KREBSFORSCHUNGSZENTRUM STIFTUNG DES ÖFFENTLICHEN RECHTS, Heidelberg (DE)

(72) Inventors: Peter Altevogt, Neckargemünd (DE); Sandra Lüttgau, Schongau (DE); Gerhard Moldenhauer, Bad Arolsen (DE); John Hazin, Heidelberg (DE)

(73) Assignee: DEUTSCHES KREBSFORSCHUNGSZENTRUM STIFTUNG DES ÖFFENTLICHEN RECHTS (DE)

( * ) Notice: Subject to any disclaimer, the term of this patent is extended or adjusted under 35 U.S.C. 154(b) by 9 days.

(21) Appl. No.: 15/515,722

(22) PCT Filed: Sep. 28, 2015

(86) PCT No.: PCT/EP2015/072279
§ 371 (c)(1),
(2) Date: Mar. 30, 2017

(87) PCT Pub. No.: WO2016/050702
PCT Pub. Date: Apr. 7, 2016

(65) Prior Publication Data
US 2017/0306015 A1    Oct. 26, 2017

(30) Foreign Application Priority Data
Sep. 30, 2014   (EP) .................................... 14003383

(51) Int. Cl.
| | |
|---|---|
| C07K 16/28 | (2006.01) |
| C07K 16/30 | (2006.01) |
| A61K 39/395 | (2006.01) |
| A61K 31/337 | (2006.01) |
| A61K 31/277 | (2006.01) |
| A61K 31/365 | (2006.01) |
| A61K 31/407 | (2006.01) |
| A61K 31/513 | (2006.01) |
| A61K 31/535 | (2006.01) |
| A61K 31/555 | (2006.01) |
| A61K 31/704 | (2006.01) |
| A61K 31/7048 | (2006.01) |
| A61K 33/24 | (2019.01) |
| A61K 45/06 | (2006.01) |
| G01N 33/574 | (2006.01) |
| A61K 38/15 | (2006.01) |
| A61K 47/68 | (2017.01) |
| A61K 39/00 | (2006.01) |

(52) U.S. Cl.
CPC ........ *C07K 16/2803* (2013.01); *A61K 31/277* (2013.01); *A61K 31/337* (2013.01); *A61K 31/365* (2013.01); *A61K 31/407* (2013.01); *A61K 31/513* (2013.01); *A61K 31/555* (2013.01); *A61K 31/704* (2013.01); *A61K 31/7048* (2013.01); *A61K 33/24* (2013.01); *A61K 38/15* (2013.01); *A61K 39/39558* (2013.01); *A61K 45/06* (2013.01); *A61K 47/6849* (2017.08); *G01N 33/57492* (2013.01); *A61K 2039/505* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,223,409 A | 6/1993 | Ladner et al. | |
| 5,225,539 A | 7/1993 | Winter | |
| 5,585,089 A | 12/1996 | Queen et al. | |
| 2005/0074426 A1 | 4/2005 | Corti et al. | |

(Continued)

FOREIGN PATENT DOCUMENTS

| | | |
|---|---|---|
| WO | 9002809 A1 | 3/1990 |
| WO | 9012592 A1 | 11/1990 |

(Continued)

OTHER PUBLICATIONS

Paul, Fundamental Immunology, 3rd Edition, 1993, pp. 292-295.*

(Continued)

*Primary Examiner* — Hong Sang
(74) *Attorney, Agent, or Firm* — Lathrop Gage LLP; Andrew T. Wilkins

(57) ABSTRACT

The present disclosure relates to a binding molecule binding to L1, which is capable of binding to the same L1 epitope recognized by the monoclonal antibody L1-OV52.24, and/or which competes with the monoclonal antibody L1-OV52.24 for binding to L1, wherein the variable part of the light chain of L1-OV52.24 comprises the sequence according to SEQ ID No: 1 or wherein the light chain is encoded by SEQ ID No: 3, and wherein the variable part of the heavy chain of L1-OV52.24 comprises the sequence according to SEQ ID No: 2 or wherein the heavy chain is encoded by SEQ ID No: 4, nucleic acids encoding the binding molecules, uses thereof and pharmaceutical compositions comprising the binding molecules.

Figure 1:
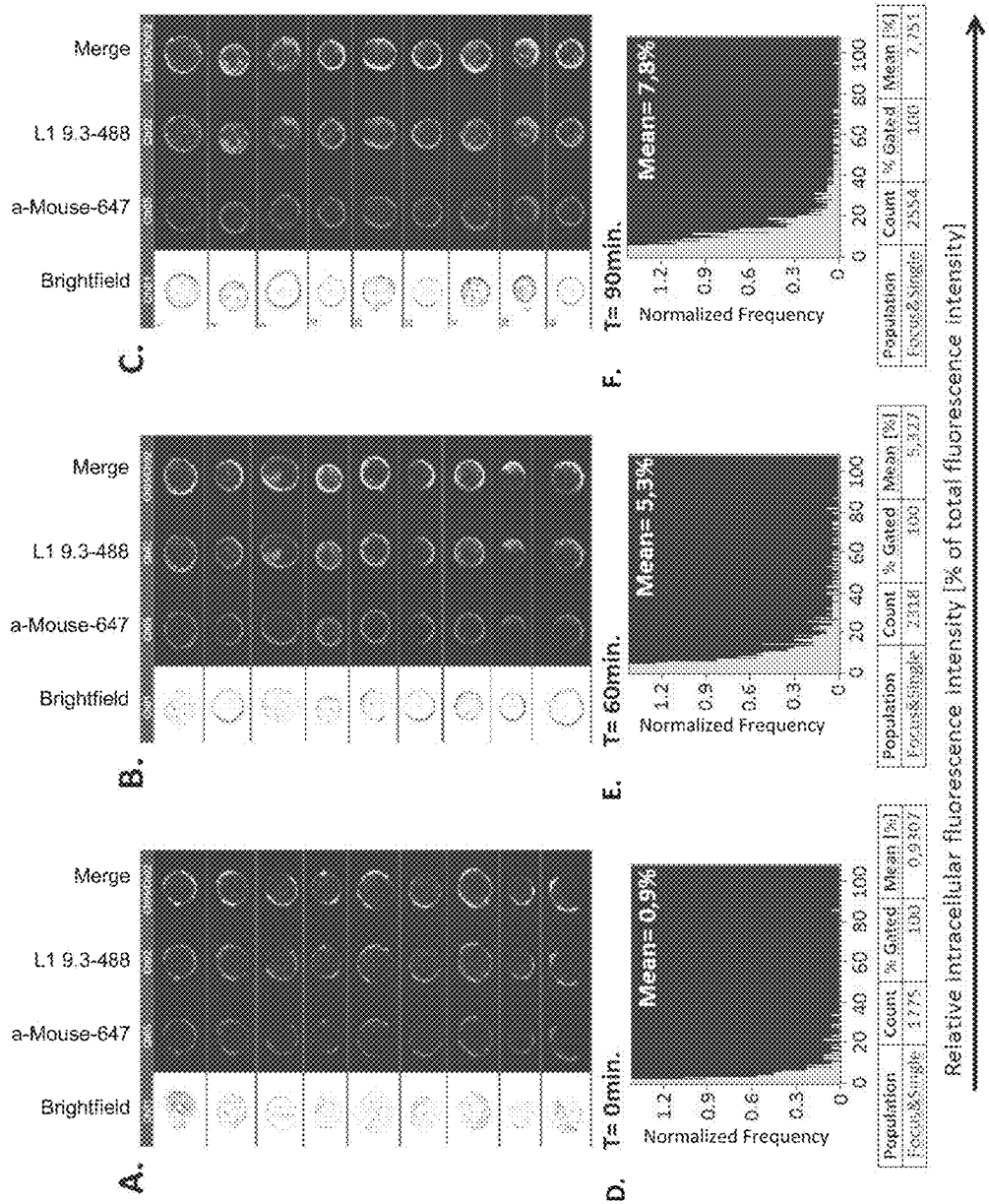

25 Claims, 8 Drawing Sheets
Specification includes a Sequence Listing.

(56) References Cited

U.S. PATENT DOCUMENTS

| | | | | |
|---|---|---|---|---|
| 2009/0162355 A1* | 6/2009 | Gast | ............... | A61N 5/0613 424/135.1 |
| 2011/0171290 A1* | 7/2011 | Altevogt | ............ | C07K 16/2803 424/450 |
| 2015/0376276 A1* | 12/2015 | Lewis | ................ | C07K 16/2803 424/133.1 |

FOREIGN PATENT DOCUMENTS

| WO | 9117271 A1 | 11/1991 |
|---|---|---|
| WO | 9201047 A1 | 1/1992 |
| WO | 9209690 A2 | 6/1992 |
| WO | 9215679 A1 | 9/1992 |
| WO | 9218619 A1 | 10/1992 |
| WO | 9220791 A1 | 11/1992 |
| WO | 9301288 A1 | 1/1993 |
| WO | 9404189 A1 | 3/1994 |
| WO | 9840052 A1 | 9/1998 |
| WO | 2004003183 A1 | 1/2004 |
| WO | 2004067038 A1 | 8/2004 |
| WO | 2007030642 A2 | 3/2007 |
| WO | WO 2008/052187 A2 | 5/2008 |
| WO | 2008151819 A2 | 12/2008 |

OTHER PUBLICATIONS

Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Berglund et al, Protein Science, 2008, 17:606-613.*
Doberstein et al. (2014) "Antibody therapy to human L1CAM in a transgenic mouse model blocks local tumor growth but induces EMT," International journal of cancer. 136(5): E326-E339.
Fuchs et al. (1991) "Targeting recombinant antibodies to the surface of *Escherichia coli*: fusion to a peptidoglycan associated lipoprotein," Bio/Technology 9:1370-1372.
Galluzzi et al. (2012) "Trial Watch: Monoclonal antibodies in cancer therapy," Oncoimmunology. 1(1):28-37.
Gouveia et al. (2007) "Production and purification of functional truncated soluble forms of human recombinant L1 cell adhesion glycoprotein from Spodoptera frugiperda Sf9 cells," Protein Expr Purif. 52:182-193.
Griffiths et al. (1993) "Human anti-self antibodies with high specificity from phage display libraries," EMBO J. 12:725-734.
Hay et al. (1992) "Bacteriophage cloning and *Escherichia coli* expression of a human IgM Fab," Hum. Antibod. Hybridomas. 3:81-85.
Huse et al. (1989) "Generation of a large combinatorial library of the immunoglobulin repertoire in phage lambda," Science. 246:1275-1281.
Langer (1990) "New methods of drug delivery," Science. 249:1527-1533.
Long et al. (2001) "The role of endocytosis in regulating L1-mediated adhesion," The Journal of biological chemistry. 276(2)1285-1290.
Novak-Hofer et al. (1994) "Internalization and degradation of monoclonal antibody chCE7 by human neuroblastoma cells," International journal of cancer 57(3):427-432.
Oleszewski et al. (2000) "Characterization of the L1-neurocan binding site: Implications for L1-L1 homophilic binding," J.Biol. Chem. 275:34478-34485.
Pastan et al. (2007) "Immunotoxin treatment of cancer," Annu. Rev. Med. 58:221-237.
Presta (2008) "Molecular engineering and design of therapeutic antibodies," Curr Opin Immunol. 20(4):460-470.
Reichert (2011) "Antibody-based therapeutics to watch in 2011," MAbs. 3(1):76-99.
Reichert (2012) Marketed therapeutic antibodies compendium, MAbs. 4(3):413-415.
Reichert (2014) "Antibodies to watch in 2014: mid-year update," MAbs. 6(4):799-802.
Schaefer et al. (1999) "Activation of the MAPK signal cascade by the neural cell adhesion molecule L1 requires L1 internalization," The Journal of biological chemistry. 274(53):37965-37973.
Schaefer et al. (2002) "L1 endocytosis is controlled by a phosphorylation-dephosphorylation cycle stimulated by outside-in signaling by L1," The Journal of cell biology. 157(7):1223-1232.
Winter et al. (1991) "Man-made antibodies," Nature. 349:293-299.
Wolterink et al. (2010) "Therapeutic antibodies to human L1CAM: functional characterization and application in a mouse model for ovarian carcinoma," Cancer Res. 70(6):2504-2515.
Wu et al. (1987) "Receptor-mediated in vitro gene transformation by a soluble DNA carrier system," J. Biol. Chem. 262:4429-4432.
Wu et al. (2005) "Arming antibodies: prospects and challenges for immunoconjugates," Nature Biotechnol. 23:1137-1146.

* cited by examiner

B.

BINDING MOLECULES, ESPECIALLY ANTIBODIES, BINDING TO L1CAM (CD171)

RELATED APPLICATIONS

This application is a 35 U.S.C. § 371 filing of International Application No. PCT/EP2015/072279, filed Sep. 28, 2015, which claims priority to European Patent Application No. 14003383.8, filed Sep. 30, 2014, each of which is incorporated herein by reference in its entirety.

The present invention relates to a binding molecule binding to L1, which is capable of binding to the same L1 epitope recognized by the monoclonal antibody L1-OV52.24, and/or which competes with the monoclonal antibody L1-OV52.24 for binding to L1, wherein the variable part of the light chain of L1-OV52.24 comprises the sequence according to SEQ ID No: 1 or wherein the light chain is encoded by SEQ ID No: 3, and wherein the variable part of the heavy chain of L1-OV52.24 comprises the sequence according to SEQ ID No: 2 or wherein the heavy chain is encoded by SEQ ID No: 4, nucleic acids encoding the binding molecules, uses thereof and pharmaceutical compositions comprising the binding molecules.

Monoclonal antibodies (mAbs) have emerged as a new and important pillar for cancer therapy [1]. During the past two decades molecular biology has provided means to create chimeric, humanized or fully human antibodies for the treatment of major malignant diseases [2]. To date, many antibodies and antibody-conjugates are approved as cancer therapeutics for marketing in Europe and the United States [3, 4]. They comprise unmodified antibodies, antibody-drug conjugates as well as conjugates with radionuclides and a bispecific antibody [5]. However, it is quite known that mAbs to a given cancer antigen may differ in their ability to target the cancer cell.

In recent work we have shown that L1CAM (also called L1) may be an excellent target molecule for human cancers. L1CAM is overexpressed in many human cancers, confers bad prognosis and augments cell motility, invasion and metastasis. Results from xenograft [6] and human L1CAM transgenic mouse [7] models have suggested that L1CAM mAb L1-9.3 (also called mAb 9.3) might be a promising tool for cancer therapy. This mAb binds to the 1. Ig-like domain of the L1CAM molecule and has good ADCC-functions [6]. Recent results have shown that this mAb in its IgG2a version is well suited to activate the immune system and recruit immune effector cells leading to the elimination of cancer cells [6, 7]. Thus, there is ample evidence that this mAb is particularly suited for ADCC-dependent effector mechanisms that represents an important arm of mAb-dependent tumor therapy.

WO 2008/151819 [12] discloses the anti-L1 antibody 9.3 which binds to an epitope within the first Ig domain of L1.

Recent advances in antibody-drug conjugates ask for mAbs having the feature of rapid internalization. It is quite known that binding of L1CAM specific antibodies will lead to L1CAM internalization followed by recycling or degradation of the target molecule [8]. The feature of internalization the L1CAM molecule has in common with many other cell surface molecules. In fact, it is known that L1CAM internalization is required for signaling and regulation of L1CAM mediated cell adhesion [9-11].

Antibody-induced internalization of L1CAM has been reported in several publications (mostly using polyclonal antibodies) but no systematic investigations with mAbs have been carried out. Thus, it is presently not known whether the engagement of different epitopes on the L1CAM molecule will result in different rates of internalization. We have now generated a L1CAM specific mAb that binds to the FNIII-4-5 and is termed mAb L1-OV52.24 (or OV52.24). We made the surprising observation that this mAb has a much better internalization rate than the previously characterized mAb L1-9.3. We made the further surprising observation that mAb L1-OV52.24 has a much better internalization rate than the anti-L1CAM monoclonal antibodies 5G3 and UJ127.11, respectively. The unique properties of L1-OV52.24 will allow improved and accelerated drug delivery to cancer cells.

Even though some features of the antibody L1-OV52.24 of the invention have in part already been described, c.f. [6], the antibody itself or the sequence of the complementarity determining regions (CDR) of the antibody of the invention has never been published or made available to the public.

Many therapeutically active agents are only efficient within a cell. This raises a problem in case such therapeutically active agent cannot enter a cell in an unmodified form. Therefore, there is a need for binding agents, such as monoclonal antibodies or antigen-binding fragments thereof which are efficiently internalized into tumor cells and which can therefore target agents linked to binding agent into a tumor cell.

It was found that monoclonal antibody L1-OV52.24 surprisingly exhibits a quick and efficient internalization into L1-bearing mammalian cells, as determined both by microscopic analysis and by imaging flow cytometry of such cells incubated with L1-OV52.24 for 40, 60, 70 or 90 minutes, respectively, as shown in the examples.

Therefore, such monoclonal antibodies, or other binding molecules, such as antibodies, which bind to L1 and which bind to same epitope of L1 recognized by L1-OV52.24 are surprisingly advantageous in the field of biotechnological research, diagnosis or therapy. In particular, an active agent may be linked to a binding molecule of the invention, which is taken up into the cell by internalization. Such active agent may then exert the desired effect in the cell, such as a cytotoxic or cytostatic effect.

In one embodiment, the present invention relates to a binding molecule binding to L1, which is capable of binding to the same L1 epitope recognized by the monoclonal antibody L1-OV52.24, wherein the variable part of the light chain of L1-OV52.24 comprises, preferably has the sequence according to SEQ ID No: 1 or wherein the light chain is encoded by SEQ ID No: 3, and wherein the variable part of the heavy chain of L1-OV52.24 comprises, preferably has the sequence according to SEQ ID No: 2 or wherein the heavy chain is encoded by SEQ ID No: 4.

SEQ ID No: 1 relates to the VJ domain, i.e. the variable part, of the light chain of L1-OV52.24. The constant domain of the light chain is known in the art and its murine cDNA sequence is depicted below.

SEQ ID No: 2 relates to the VDJ domain, i.e. the variable part of the heavy chain of L1-OV52.24. The constant domain of the heavy chain is known in the art and its murine cDNA sequence is depicted below.

L1, also known as L1CAM, is a transmembrane protein; it is a neuronal cell adhesion molecule, member of the L1 protein family, of 200-220 kDa, and involved in axon guidance and cell migration with a strong implication in treatment-resistant cancers. L1 according to the present invention is preferably understood as mammalian L1 protein, more preferably as human or mouse L1 protein. The Genbank entry for human L1 protein is NP_000416, and the Genbank entry for the murine L1 protein is NP_032504. L1CAM has also been designated CD171.

An epitope is the part of an antigen that is recognized by antibodies or related binding molecules. For example, the epitope is the specific piece of the antigen that an antibody binds to. Epitopes may be conformational epitopes or linear epitopes. A conformational epitope is composed of discontinuous sections of the antigen's amino acid sequence. These epitopes interact with the paratope based on the 3-D surface features and shape or tertiary structure of the antigen. The proportion of epitopes that are conformational is unknown.

It was shown in the Examples that L1-OV52.24 binds to and recognizes an epitope within the fibronectin III 4-5 domain of L1. Methods for determining an epitope bound and recognized by a binding molecule are described in the prior art (Wolterink et. al., Cancer Res. (2010), 70: 2504-2515) and in the Examples. As shown in the Examples, a recognized epitope is preferably determined by constructing a series of L1-Fc proteins carrying distinct Ig domains. For fine mapping according to the Examples, recombinant V5-tagged L1 fragments can be used, as for example as described in Gouveia et al. (Protein Expr. Purif. (2007) 52: 182-193). The recombinant proteins can be used in ELISA or in Western blot analysis for epitope mapping. mAbs L1-OV52.24 reacted with the 4-5FNIII domain of L1. In general, methods for determining the epitope of a given antibody are known in the art and include the preparation of synthetic linear peptides of a given region of interest and the subsequent testing whether the antibody binds to said peptides (see Epitope Mapping, A practical approach, Oxford University Press 2001, Editors: Olwyn Westwood and Frank Hay). Alternatively, different recombinant proteins covering the region of interest can be produced and tested for the binding of the antibody (Oleszewski, M., Gutwein, P., von der Lieth, W., Rauch, U., Altevogt, P. Characterization of the L1-neurocan binding site. Implications for L1-L1 homophilic binding. J. Biol. Chem. 275: 34478-34485 (2000)).

In a further embodiment, the present invention relates to a binding molecule which competes with the monoclonal antibody L1-OV52.24 for binding to L1, wherein the variable part of the light chain of L1-OV52.24 comprises, preferably has the sequence according to SEQ ID No: 1 or wherein the light chain is encoded by SEQ ID No: 3, and wherein the heavy chain of L1-OV52.24 comprises, preferably has the sequence according to SEQ ID No: 2 or wherein the heavy chain is encoded by SEQ ID No: 4.

Competition may be determined by assays known to a skilled person, such as Competition binding assays.

The protein sequence of the light chain (VJ domain, without constant domain; i.e. the variable part) of L1-OV52.24 is as follows:

```
                                                        (SEQ ID No: 1)
  1 DIVMTQSQKF MSTSVGDRVS VTCKASQNVG TNVAWYQQKP GHSPKALIYS

51 TSYRYSGVPD RFTGSGSGTD FTLTIRNVQS EDLAEYFCQQ YNTYPYTFGG

101 GTKLEIK
```

The sequences of the CDRs of the light chain (VJ domain) of L1-OV52.24 according to Kabat are as follows:

```
                                        (SEQ ID No: 5)
         CDR-L1 (or LCDR1): KASQNVGTNVA (SEQ ID No: 6)
         CDR-L2 (or LCDR2): STSYRYS (SEQ ID No: 7)
         CDR-L3 (or LCDR3): QQYNTYPYT
```

The protein sequence of the heavy chain (VDJ domain, without constant domain; i.e. the variable part) of L1-OV52.24 is as follows:

```
                                                        (SEQ ID No: 2)
  1 EVQLQQSGAE LVRPGALVKL SCKASGFNIK DYYMQWVKQR PEQGLEWIGW

51 IDPENGKTVF DPKFRGKASI SADTSSNTAY LQLSSLTSED TAVYYCARWN

101 PLAFWGQGTL VTVSS
```

The sequences of the CDRs according to Kabat are shown underlined.

The sequences of the CDRs of the heavy chain (VDJ domain) of L1-OV52.24 according to Kabat are as follows:

```
                                        (SEQ ID No: 8)
         CDR-H1 (or HCDR1): FNIKDYYMQ (SEQ ID No: 9)
         CDR-H2 (or HCDR2): WIDPENGKTVFDPKFRG (SEQ ID No: 10)
         CDR-H3 (or HCDR3: WNPLAF
```

The cDNA sequence of the immunoglobulin genes of the L1-OV52.24 monoclonal antibody is as follows:

Code: 5'UTR (partial, i.e. as long as sequenced), Leader,
IGKV/IGKJ or IGHV/IGHD/IGHJ, *IGKC or IGHC*

Heavy chain
(SEQ ID No: 4)

*CTGCCtCATGAATATGcAAACATGAGtCTGTGATTATAAATACAgagATATCCAtA*

*CCAAACAACtTATGAgCACTGTTTTCTCTACAGTCACTGAATCTCAAgGTCCTTA*

<u>CAATGcAATGCAGCTGGGTCATCTTCTTCCTGATGGCAGTGGTTACAGGGGT</u>

<u>CAATTCA</u>GAGGTTCAGCTGCAGCAGTCTGGGGCTGAGCTTGTGAGGCCAGG

GGCCTTAGTCAAGTTGTCCTGCAAAGCTTCTGGCTTCAACATTAAAGACTAC

TATATGCAGTGGGTGAAGCAGAGGCCTGAACAGGGCCTGGAGTGGATTGG

ATGGATTGATCCTGAGAATGGTAAAACAGTTTTTGACCCGAAGTTCCGGGG

CAAGGCCAGTATATCAGCGGACACATCCTCCAACACAGCCTACCTGCAGCT

CAGCAGCCTGACATCTGAGGACACTGCCGTCTATTACTGTGCTAGATGGAA

CCCCCTTGCCTTCTGGGGCCAAGGGACTCTGGTCACTGTCTCTGCA*GCCAA*

*AACGACACCCCCATCTGTCTATCCACTGGCCCCTGGATCTGCTGCCCAAAC*

*TAACTCCATGGTGACCCTGGGATGCCTGGTCAAGGGCTATTTCCCTGAGCC*

*AGTGACAGTGACCTGGAACTCTGGATCCCTGTCCAGCGGTGTGCACACCTT*

*CCCAGCTGTCCTGGAGTCTGACCTCTACACTCTGAGCAGCTCAGTGACTGT*

*CCCCTCCAGCCCTCGGCCCAGCGAGACCGTCACCTGCAACGTTGCCCACC*

*CGGCCAGCAGCACCAAGGTGGACAAGAAAATTGTGCCCAGGGATTGTGGT*

*TGTAAGCCTTGCATATGTACAGTCCCAGAAGTATCTCTGTCTTCATCTTCC*

*CCCCAAAGCCCAAGGATGTGCTCACCATTACTCTGACTCCTAAGGTCACGT*

*GTGTTGTGGTAGACATCAGCAAGGATGATCCCGAGGTCCAGTTCAGCTGGT*

*TTGTAGATGATGTGGAGGTGCACACAGCTCAGACGCAACCCCGGGAGGAG*

*CAGTTCAACAGCACTTTCCGCTCAGTCAGTGAACTTCCCATCATGCACCAG*

*GACTGGCTCAATGGCAAGGAGTTCAAATGCAGGGTCAACAGTGCAGCTTTC*

*CCTGCCCCCATCGAGAAAACCATCTCCAAAACCAAAGGCAGACCGAAGGC*

*TCCACAGGTGTACACCATTCCACCTCCCAAGGAGCAGATGGCCAAGGATAA*

*AGTCAGTCTGACCTGCATGATAACAGACTTCTTCCCTGAAGACATTACTGTG*

*GAGTGGCAGTGGAATGGGCAGCCAGCGGAGAACTACAAGAACACTCAGCC*

*CATCATGAACACGAATGGCTCTTACTTCGTCTACAGCAAGCTCAATGTGCA*

*GAAGAGCAACTGGGAGGCAGGAAATACTTTCACCTGCTCTGTGTTACATGA*

*GGGCCTGCACAACCACCATACTGAGAAGAGCCTCTCCCACTCTCCTGGTAA*

*ATGA*

Light chain
(SEQ ID No: 3)

*TTTGATGACTGCTTTGCATAGATCCCTAGAGGCCAGCCCAGCTGCCCATGAT*

*TTATAAACCAGGTCTTTGCAGTGAGATCTGAAATACATCAGATCAGCATGGGC*

<u>ATCAAG</u>ATGGAGTCACAGACTCAGGTCTTTGTATACATGTTGCTGTGGTTGTC

<u>TGGTGTTGATGGA</u>GACATTGTGATGACCCAGTCTCAAAAATTCATGTCCACA

TCAGTAGGAGACAGGGTCAGCGTCACCTGCAAGGCCAGTCAGAATGTGGG

TACTAATGTGGCCTGGTATCAACAGAAACCAGGTCACTCTCCTAAAGCACT

GATTTACTCGACATCCTACCGGTACAGTGGAGTCCCTGATCGCTTCACAGG

CAGTGGATCTGGGACAGATTTCACTCTCACCATCCGCAATGTGCAGTCTGA

-continued

```
AGACTTGGCAGAGTACTTCTGTCAGCAATATAACACCTATCCGTACACGTTC

GGAGGGGGGACCAAGCTGGAAATAAAACGGGCTGATGCTGCACCAACTGT

ATCCATCTTCCCACCATCCAGTGAGCAGTTAACATCTGGAGGTGCCTCAGT

CGTGTGCTTCTTGAACAACTTCTACCCCAAAGACATCAATGTCAAGTGGAA

GATTGATGGCAGTGAACGACAAAATGGCGTCCTGAACAGTTGGACTGATCA

GGACAGCAAAGACAGCACCTACAGCATGAGCAGCACCCTCACGTTGACCA

AGGACGAGTATGAACGACATAACAGCTATACCTGTGAGGCCACTCACAAGA

CATCAACTTCACCCATTGTCAAGAGCTTCAACAGGAATGAGTGTTAG
```

In a preferred embodiment, the binding molecule is an anti-L1 monoclonal antibody or an antigen-binding fragment thereof.

A binding molecule is understood as polypeptide, which exhibits specific binding to the target indicated. According to the present invention, the target is the protein L1. Therefore, binding molecules of the invention specifically bind to L1. Preferably, the binding molecule is an immunoglobulin comprising molecule, i.e. comprises at least one Ig domain or an anti-L1 antibody.

"Specific binding" is understood that the binding of the binding molecule to L1 is at least 50-fold, preferably at least 100-fold stronger than the binding to a control protein such as albumin, as determined e.g. by Western Blot analysis or ELISA.

The term "anti-L1 antibody", as used herein, means any polypeptide which has structural similarity to a naturally occurring antibody and is capable of binding to L1, wherein the binding specificity is determined by the CDRs of the polypeptides.

Hence, "anti-L1 antibody" is intended to relate to an immunoglobulin-derived structure with binding to L1. The antigen-binding fragment is understood as polypeptide which comprises at least one antigen binding fragment of a full-length antibody. Antigen binding fragments consist of at least the variable domain of the heavy chain and the variable domain of the light chain, arranged in a manner that both domains together are able to bind to the specific antigen.

Monoclonal antibodies are monospecific antibodies that are identical because they are produced by one type of immune cell that are all clones of a single parent cell. "Monoclonal antibodies" and the production of monoclonal antibodies belong to the state of the art. In general, monoclonal antibodies can, for example, be prepared in accordance with the known method of Winter & Milstein (Winter, G. & Milstein, C. (1991) Nature, 349, 293-299). An alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734.

"Full length" or "complete" antibodies refer to proteins that comprise two heavy (H) and two light (L) chains inter-connected by disulfide bonds which comprise: (1) in terms of the heavy chains, a variable region and a heavy chain constant region which comprises three domains, $C_H1$, $C_H2$ and $C_H3$; and (2) in terms of the light chains, a light chain variable region and a light chain constant region which comprises one domain, $C_L$. With regard to the term "complete antibody", any antibody is meant that has a typical overall domain structure of a naturally occurring antibody (i.e. comprising a heavy chain of three or four constant domains and a light chain of one constant domain as well as the respective variable domains), even though each domain may comprise further modifications, such as mutations, deletions, or insertions, which do not change the overall domain structure. For instance, mAb L1-OV52.24 is a full length antibody.

An "antigen-binding fragment" of a monoclonal antibody is a fragment of a monoclonal antibody, which exhibits essentially the same function and specificity as the complete monoclonal antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single $F(ab')_2$ fragment containing both Fab pieces and the hinge region, including the H—H interchain disulfide bond. $F(ab')_2$ is divalent for antigen binding. The disulfide bond of $F(ab')_2$ may be cleaved in order to obtain Fab'. Moreover, the variable regions of the heavy and light chains can be fused together to form a single chain variable fragment (scFv).

As the first generation of full sized antibodies presented some problems, many of the second generation antibodies have comprised only fragments of the antibody. Variable domains (Fvs) are the smallest fragments with an intact antigen-binding domain consisting of one $V_L$ and one $V_H$. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides.

A recombinant antibody fragment is the single-chain Fv (scFv) fragment. In general, it has a high affinity for its antigen and can be expressed in a variety of hosts. These and other properties make scFv fragments not only applicable in medicine, but also of potential for biotechnological applications. As detailed above, in the scFv fragment the $V_H$ and $V_L$ domains are joined with a hydrophilic and flexible peptide linker, which improves expression and folding efficiency. Usually linkers of about 15 amino acids are used, of which the $(Gly_4Ser)_3$ linker has been used most frequently. scFv molecules might be easily proteolytically degraded, depending on the linker used. With the development of genetic engineering techniques these limitations could be practically overcome by research focussed on improvement of function and stability. An example is the generation of disulfide-stabilized (or disulfide-linked) Fv fragments where the $V_H$-$V_L$ dimer is stabilized by an interchain disulfide bond. Cysteines are introduced at the interface between the $V_L$ and $V_H$ domains, forming a disulfide bridge, which holds the two domains together.

Dissociation of scFvs results in monomeric scFvs, which can be complexed into dimers (diabodies), trimers (triabodies) or larger aggregates such as TandAbs and Flexibodies.

Antibodies with two binding domains can be created either through the binding of two scFv with a simple polypeptide link (scFv)2 or through the dimerization of two monomers (diabodies). The simplest designs are diabodies that have two functional antigen-binding domains that can be either the same, similar (bivalent diabodies) or have specificity for distinct antigens (bispecific diabodies).

Also, antibody formats comprising four variable domains of heavy chains and four variable domains of light chains have been developed. Examples of these include tetravalent bispecific antibodies (TandAbs and Flexibodies, Affimed Therapeutics AG, Heidelberg. Germany). In contrast to a bispecific diabody, a bispecific TandAb is a homodimer consisting of only one polypeptide. Because the two different chains, a diabody can build three different dimers only one of which is functional. Therefore, it is simpler and cheaper to produce and purify this homogeneous product. Moreover, the TandAb usually shows better binding properties (possessing twice the number of binding sites) and increased stability in viva Flexibodies are a combination of scFv with a diabody multimer motif resulting in a multivalent molecule with a high degree of flexibility for joining two molecules which are quite distant from each other on the cell surface. If more than two functional antigen-binding domains are present and if they have specificity for distinct antigens, the antibody is multispecific.

In summary, specific immunoglobulins, into which particular disclosed sequences may be inserted or, in the alternative, form the essential part of, include but are not limited to the following binding molecules which form particular embodiments of the present invention: a Fab (monovalent fragment with variable light ($V_L$), variable heavy ($V_H$), constant light ($C_L$) and constant heavy 1 ($C_H1$) domains), a F(ab')2 (bivalent fragment comprising two Fab fragments linked by a disulfide bridge or alternative at the hinge region), a Fv ($V_L$ and $V_H$ domains), a scFv (a single chain Fv where $V_L$ and $V_H$ are joined by a linker, e.g., a peptide linker), a bispecific antibody molecule (an antibody molecule comprising a polypeptide as disclosed herein linked to a second functional moiety having a different binding specificity than the antibody, including, without limitation, another peptide or protein such as an antibody, or receptor ligand), a bispecific single chain Fv dimer, a diabody, a triabody, a tetrabody, a minibody (a scFv joined to a $C_H3$).

Certain binding molecules or antigen-binding fragments of monoclonal antibodies including, but not limited to, Fv, scFv, diabody molecules or domain antibodies (Domantis) may be stabilized by incorporating disulfide bridges to line the VH and VL domains. Bispecific antibodies may be produced using conventional technologies, specific methods of which include production chemically, or from hybrid hybridomas) and other technologies including, but not limited to, the BiTE™ technology (molecules possessing antigen binding regions of different specificity with a peptide linker) and knobs-into-holes engineering.

Accordingly, the binding molecule or antigen-binding fragment of a monoclonal antibody may be a Fab, a Fab', a F(ab')2, a Fv, a disulfide-linked Fv, a scFv, a (scFv)$_2$, a bivalent antibody, a bispecific antibody, a multispecific antibody, a diabody, a triabody, a tetrabody or a minibody.

In another preferred embodiment, the binding molecule is a human antibody, chimeric antibody or a humanized antibody. A chimeric antibody is an antibody in which at least one region of an immunoglobulin of one species is fused to another region of an immunoglobulin of another species by genetic engineering in order to reduce its immunogenicity. For example murine $V_L$ and $V_H$ regions may be fused to the remaining part of a human immunoglobulin. A particular type of chimeric antibodies are humanized antibodies. Humanised antibodies are produced by merging the DNA that encodes the CDRs of a non-human antibody with human antibody-producing DNA. The resulting DNA construct can then be used to express and produce antibodies that are usually not as immunogenic as the non-human parenteral antibody or as a chimeric antibody, since merely the CDRs are non-human. Further, the antibody may be human.

The use of a human or at least humanized antibody is preferred for applications in the human, e.g. for the prevention, treatment or diagnosis in vivo.

In one preferred embodiment of the present invention, the binding molecule, in particular monoclonal antibody, comprises a heavy chain immunoglobulin constant domain selected from the group consisting of: a human IgM constant domain, a human IgGI constant domain, a human IgG2 constant domain, a human IgG3 constant domain, a human IgG4 constant domain, a human IgE constant domain, and a human IgA constant domain.

As detailed above in the context with the binding molecule, preferably monoclonal antibody of the present invention, each heavy chain of a naturally occurring antibody has two regions, the constant region and the variable region. There are five types of mammalian immunoglobulin heavy chain: γ, δ, α, μ and ε, which define classes of immunoglobulins IgM, IgD, IgG, IgA and IgE, respectively.

There are here are four IgG subclasses (IgG1, 2, 3 and 4) in humans, named in order of their abundance in serum (IgG1 being the most abundant). Even though there is about 95% similarity between their Fc regions of the IgG subclasses, the structure of the hinge regions are relatively different. This region, between the Fab arms (Fragment antigen binding) and the two carboxy-terminal domains $C_H2$ and $C_H3$ of both heavy chains, determines the flexibility of the molecule. The upper hinge (towards the amino-terminal)

segment allows variability of the angle between the Fab arms (Fab-Fab flexibility) as well as rotational flexibility of each individual Fab. The flexibility of the lower hinge region (towards the carboxy-terminal) directly determines the position of the Fab-arms relative to the Fc region (Fab-Fc flexibility). Hinge-dependent Fab-Fab and Fab-Fc flexibility may be important in triggering further effector functions such as complement activation and Fc receptor binding. Accordingly, the structure of the hinge regions gives each of the four IgG classes their unique biological profile.

The length and flexibility of the hinge region varies among the IgG subclasses. The hinge region of IgG1 encompasses amino acids 216-231 and since it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, it is relatively short and contains a rigid poly-proline double helix, stabilised by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3 the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2.

Therefore, in a yet further preferred embodiment, the binding molecule is selected from the group consisting of a single chain antibody, preferably selected from an scFv and a multimer of scFv, like a diabody, triabody or tetrabody, an antibody fragment, preferably a Fab, a tandab, a flexibody and a bispecific antibody.

In a yet further preferred embodiment, the binding molecule is a chimeric antibody, a humanized antibody, or a human antibody or an antigen-binding fragment thereof.

As it can be taken from the examples, the epitope of the antibody L1-OV52.24 is within the fibronectin domain III 4-5 of L1. Therefore also the epitope of the binding molecules, in particular monoclonal antibodies or antigen-binding fragments thereof of the invention is preferably within fibronectin domain III 4-5 of L1.

Therefore, in a preferred embodiment, the epitope is within the fibronectin domain III 4-5 (FN III 4-5) of L1.

L1-OV52.24 has the following CDR sequences: KASQNVGTNVA (LCDR1; SEQ ID No: 5), STSYRYS (LCDR2; SEQ ID No: 6), QQYNTYPYT (LCDR3; SEQ ID No: 7), FNIKDYYMQ (HCDR1; SEQ ID No: 8), WIDPENGKTVFDPKFRG (HCDR2; SEQ ID No: 9), and WNPLAF (HCDR3; SEQ ID No: 10).

The above mentioned sequences show the CDRs of the monoclonal antibody L1-OV52.24 determined according to the method of Kabat, which is generally known in the art.

Therefore, in a preferred embodiment, the binding molecule is an anti-L1 monoclonal antibody or antigen-binding fragment thereof, wherein at least one of the complementarity determining regions (CDRs) of the anti-L1 monoclonal antibody or antigen-binding fragment thereof
a) has one of the sequences selected from KASQNVGTNVA (SEQ ID No: 5), STSYRYS (SEQ ID No: 6), QQYNTYPYT (SEQ ID No: 7), FNIKDYYMQ (SEQ ID No: 8), WIDPENGKTVFDPKFRG (SEQ ID No: 9), and WNPLAF (SEQ ID No: 10), or b) has a sequence which, in comparison to the sequences mentioned under a) has at least one conservative amino acid exchange.

Such a monoclonal antibody or antibody-binding fragment thereof of the invention can, e.g. be produced by CDR grafting or by recombinant production of the antibody. Such methods are known in the art (see e.g. Queen, U.S. Pat. No. 5,585,089 and Winter, U.S. Pat. No. 5,225,539, Cabilly U.S. Pat. No. 4,816,567).

Also the sequences of the CDRs may be altered, preferably by exchanges leading to a conservative amino acid exchange.

In general, manipulations may result in alterations in the FR as well as the CDR regions and include exchanges, deletions and insertion of residues. The alterations may be induced by random or directed mutagenesis. An antibody phage display system, as described before, may be employed for the selection of mutants with desired and/or improved properties.

In a preferred embodiment, the binding molecule of the invention is characterized in that the binding molecule is an anti-L1 monoclonal antibody or antigen-binding fragment thereof, and comprises the complementarity determining regions (CDRs) QQYNTYPYT (SEQ ID No: 7) and WNPLAF (SEQ ID No: 10), wherein optionally one or more conservative amino acid exchanges are present.

SEQ ID No: 7 represents the LCDR3 sequence and SEQ ID No: 10 represents the HCDR3 sequence of L1-OV52.24. LCDR3 and HCDR3 are known to be important for the binding properties for an antibody.

In a more preferred embodiment, the binding molecule of the invention is characterized in that the binding molecule is an anti-L1 monoclonal antibody or antigen-binding fragment thereof, and wherein the anti-L1 monoclonal antibody or antigen-binding fragment thereof comprises the complementarity determining regions (CDRs) KASQNVGTNVA (SEQ ID No: 5), STSYRYS (SEQ ID No: 6), QQYNTYPYT (SEQ ID No: 7), FNIKDYYMQ (SEQ ID No: 8), WIDPENGKTVFDPKFRG (SEQ ID No: 9), and WNPLAF (SEQ ID No: 10),
wherein optionally one or more conservative amino acid exchanges are present.

In a preferred embodiment, no conservative amino acid exchanges are present.

In an even more preferred embodiment, the binding molecule of the invention is characterized in that the binding molecule is an anti-L1 monoclonal antibody or antigen-binding fragment thereof, and wherein the anti-L1 monoclonal antibody or antigen-binding fragment thereof comprises the complementarity determining regions (CDRs) KASQNVGTNVA (LCDR1; SEQ ID No: 5), STSYRYS (LCDR2; SEQ ID No: 6), QQYNTYPYT (LCDR3; SEQ ID No: 7), FNIKDYYMQ (HCDR1; SEQ ID No: 8), WIDPENGKTVFDPKFRG (HCDR2; SEQ ID No: 9), and WNPLAF (HCDR3; SEQ ID No: 10),
wherein optionally one or more conservative amino acid exchanges are present.

In a preferred embodiment, no conservative amino acid exchanges are present.

In a further preferred embodiment, the anti-L1 monoclonal antibody or antigen-binding fragment thereof is an IgG1 antibody or antigen-binding fragment thereof.

In another preferred embodiment, the binding molecule of the invention comprises
a) at least one of the sequences selected from KASQNVGTNVA (SEQ ID No: 5), STSYRYS (SEQ ID No: 6), QQYNTYPYT (SEQ ID No: 7), FNIKDYYMQ (SEQ ID No: 8), WIDPENGKTVFDPKFRG (SEQ ID No: 9), and WNPLAF (SEQ ID No: 10), or b) comprises a sequence which, in comparison to the sequences mentioned under a), has at least one conservative amino acid exchange.

In a further preferred embodiment, the binding molecule of the invention comprises the sequences QQYNTYPYT (SEQ ID No: 7) and WNPLAF (SEQ ID No: 10), wherein optionally one or more conservative amino acid exchanges are present.

In an even more preferred embodiment, the binding molecule of the invention comprises the sequences KASQNVGTNVA (SEQ ID No: 5), STSYRYS (SEQ ID No: 6), QQYNTYPYT (SEQ ID No: 7), FNIKDYYMQ (SEQ ID No: 8), WIDPENGKTVFDPKFRG (SEQ ID No: 9), and WNPLAF (SEQ ID No: 10), wherein optionally one or more conservative amino acid exchanges are present.

In a preferred embodiment, no conservative amino acid exchanges are present.

In a preferred embodiment, the binding molecule of the invention is an anti-L1 monoclonal antibody comprising the complementarity determining regions (CDRs) KASQNVGTNVA (SEQ ID No: 5), STSYRYS (SEQ ID No: 6), QQYNTYPYT (SEQ ID No: 7), FNIKDYYMQ (SEQ ID No: 8), WIDPENGKTVFDPKFRG (SEQ ID No: 9), and WNPLAF (SEQ ID No: 10), or an antigen-binding fragment thereof.

In a preferred embodiment, the binding molecule of the invention is an anti-L1 monoclonal antibody comprising the complementarity determining regions (CDRs) KASQNVGTNVA (LCDR1; SEQ ID No: 5), STSYRYS (LCDR2; SEQ ID No: 6), QQYNTYPYT (LCDR3; SEQ ID No: 7), FNIKDYYMQ (HCDR1; SEQ ID No: 8), WIDPENGKTVFDPKFRG (HCDR2; SEQ ID No: 9), and WNPLAF (HCDR3; SEQ ID No: 10), or an antigen-binding fragment thereof.

It is preferred that a binding molecule of the invention exhibits a strong affinity to L1. It was found that L1-OV52.24 exhibits an affinity of KD (M)=$2.41*10^{-9}$ for L1.

Affinity to L1 may be determined by methods known in the art, as for example by surface plasmon resonance. The binding analysis for L1-OV52.24 was performed using a BIAcore 3000 equipped with a CM5 sensor chip. Briefly, a BIAcore CM5 chip was activated with EDC/NHS and various levels of L1-Fc were captured onto the activated surface. The remaining active sites were blocked by ethanolamine/HCl. L1-OV52.24 was bound to the L1-Fc surface and allowed to dissociate over time. The association and dissociation phases for each injection over each density surface were subjected to kinetic analysis.

Therefore, in a yet further preferred embodiment, the binding molecule of the invention, preferably monoclonal antibody or antigen-binding fragment thereof, binds L1 with an affinity (KD) of at least $10^{-9}$, preferably of at least $10^{-10}$ or $10^{-11}$.

Figure 6:
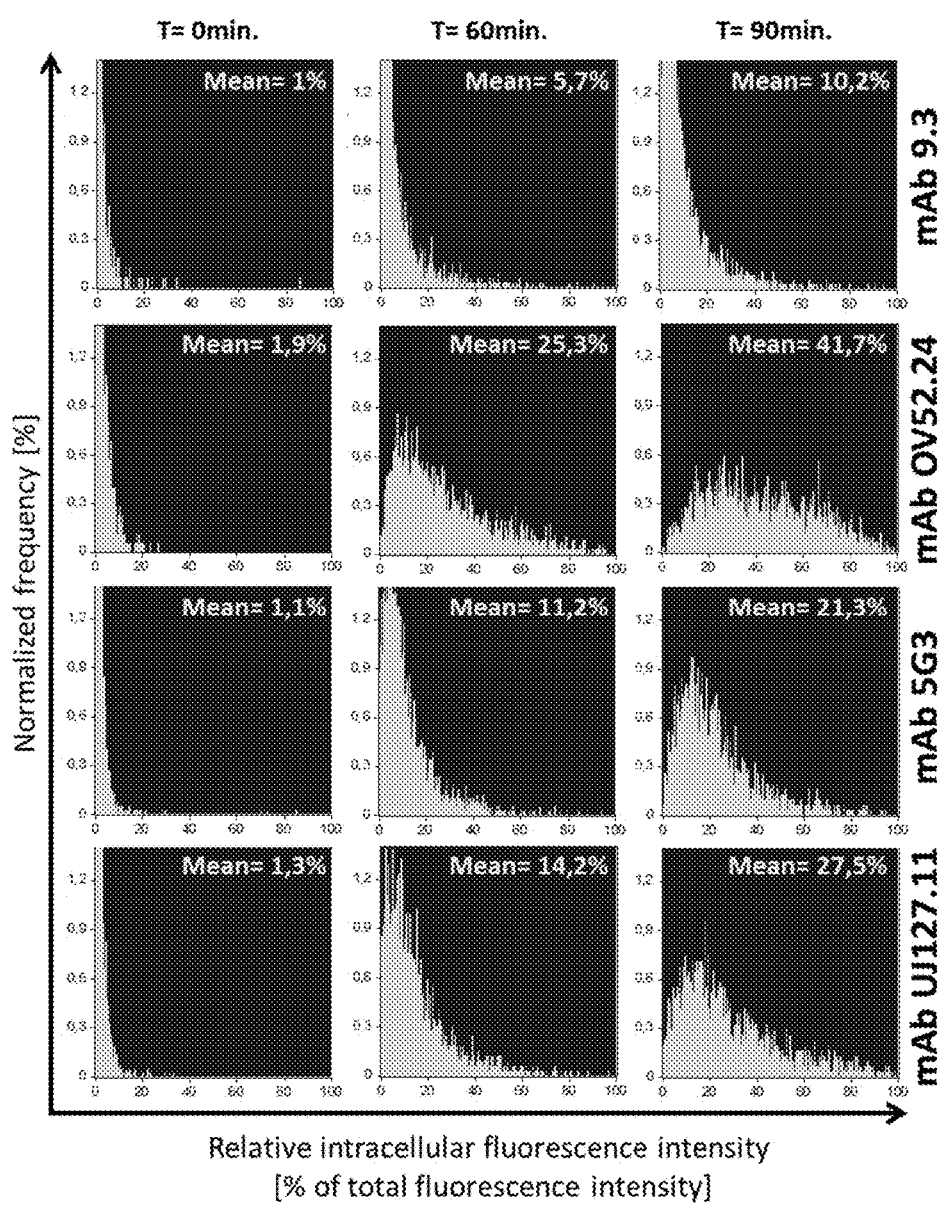

It was surprisingly found that L1-OV52.24 is efficiently internalized into SKOV3ip cells after 40, 60, 70 or 90 minutes of incubation, as shown in the Examples and Figures, whereas comparative anti-L1 monoclonal antibody 9.3 is internalized only to a small extent. Internalization may be determined using a binding molecule which is linked to a suitable diagnostic compound such as a fluorescent compound. In the examples, Alexa488 was used as fluorescent dye. The quantification of internalization may be either performed by microscopic analysis and counting or by imaging flow cytometry, as described in the examples. With both methods, it was found that L1-OV52.24 was internalized at each timepoint measured at least 4-fold more efficiently than the 9.3 antibody. Further, it was surprisingly found that L1-OV52.24 was internalized more efficiently than the commercially available anti-L1CAM monoclonal antibodies 5G3 and UJ127.11 at the measured timepoints 60' and 90' (FIG. 6). The superior and surprising internalization properties of L1-OV52.24 determined in the Examples are summarized in FIG. 7. It was surprisingly found that the internalization of L1-OV52.24 at 90' is significantly higher than the internalization of any of the prior art anti-L1CAM monoclonal antibodies 9.3, 5G3 and UJ127.11, with a $p-value \leq 0.01$, respectively. Therefore, L1-OV52.24 or antigen-binding fragments thereof or binding molecules recognizing the same epitope as L1-OV52.24, are in particular suitable for delivery of a therapeutically active agent (drug delivery) or for delivery of a diagnostic compound, e.g. for imaging purposes.

In a yet further preferred embodiment, the binding molecule of the invention is internalized by a mammalian cell expressing L1, preferably wherein the cell is a mammalian tumor cell expressing L1, more preferably a SKOV3ip cell.

In a preferred embodiment, internalization by the mammalian cell expressing L1, preferably wherein the cell is a SKOV3ip cell, is determined by microscopic analysis and quantification, or by imaging flow cytometry. The methods are preferably performed as described in the Examples. In a further preferred embodiment, internalization is at least 2-fold, preferably at least 4-fold, more preferably at least 7-fold, most preferably at least 10-fold higher than the internalization of the monoclonal antibody 9.3 as described in WO 2008/151819 after 40, 60, 70 or 90 minutes of incubation. In a yet further preferred embodiment, internalization is at least 2-fold, preferably at least 4-fold higher than the internalization of the monoclonal antibody 5G3 after 60 or 90 minutes of incubation. In a yet further preferred embodiment, internalization is at least 2-fold, preferably at least 4-fold higher than the internalization of the monoclonal antibody UJ127.11 after 60 or 90 minutes of incubation.

In an even more preferred embodiment, the binding molecule of the invention is the monoclonal antibody L1-OV52.24, wherein the variable part of the light chain of L1-OV52.24 comprises, preferably has the sequence according to SEQ ID No: 1 or wherein the light chain is encoded by SEQ ID No: 3, and wherein the variable part of the heavy chain of L1-OV52.24 comprises, preferably has the sequence according to SEQ ID No: 2 or wherein the heavy chain is encoded by SEQ ID No: 3, or an antigen-binding fragment thereof.

In a preferred embodiment, the variable part of the light chain of L1-OV52.24 comprises, preferably has the sequence according to SEQ ID No: 1 and the variable part of the heavy chain of L1-OV52.24 comprises, preferably has the sequence according to SEQ ID No: 2.

The sequences SEQ ID No: 1 and 2 relate to the VJ domain; i.e. the variable part of the light chain of L1-OV52.24 and the VDJ domain; i.e. the variable part of the heavy chain of L1-OV52.24, respectively, as shown above.

Therefore, the invention relates in one embodiment to the monoclonal antibody L1-OV52.24 or an antigen-binding fragment thereof. The monoclonal antibody L1-OV52.24 is disclosed herein by the sequences of the respective variable parts of its heavy and light chains (SEQ ID No: 2 and SEQ ID No: 1, respectively) and/or the cDNAs encoding the heavy and light chains (SEQ ID No: 3 and SEQ ID No: 4, respectively).

In a particularly preferred embodiment, the binding molecule of the invention is linked to a therapeutically active substance, which allows internalization of the therapeutically active substance.

A therapeutically active substance according to the invention is understood as a compound which has a therapeutic or preventive effect in an animal, preferably mammal, even more preferably human.

In a more preferred embodiment, the therapeutically active substance has a therapeutic or preventive effect in an animal, useful for treating or preventing a tumor disease and/or a disease associated with L1 expression.

In one preferred embodiment, the therapeutically active substance is a compound useful in chemotherapy, i.e. a chemotherapeutic compound. In a preferred embodiment, the therapeutically active substance is a cytotoxic or cytostatic compound.

Therefore, in one embodiment, the invention relates to a binding molecule of the invention linked to a therapeutically active substance, preferably to
a chemotherapeutic compound, preferably selected from an alkylating agent,
antineoplastic antibiotic, antimetabolite, and a natural source derivative,
a cytotoxic compound,
a cytostatic compound,
a cytokine, a nanoparticle, or
a radionuclide.

Suitable cytokines are for example TNFalpha, IL-2 and IL-12.

Suitable chemotherapeutic compounds are known in the art. These compounds fall into several different categories, including, for example, alkylating agents, antineoplastic antibiotics, antimetabolites, and natural source derivatives.

Examples of alkylating agents that can be used in the invention include busulfan, caroplatin, carmustine, chlorambucil, cisplatin, cyclophosphamide (i.e., cytoxan), dacarbazine, ifosfamide, lomustine, mecholarethamine, melphalan, procarbazine, streptozocin, and thiotepa.

Examples of antineoplastic antibiotics include bleomycin, dactinomycin, daunorubicin, doxorubicin, idarubicin, mitomycin (e.g., mitomycin C), mitoxantrone, pentostatin, and plicamycin.

Examples of antimetabolites include fluorodeoxyuridine, cladribine, cytarabine, floxuridine, fludarabine, flurouracil (e.g., 5-fluorouracil (5FU)), gemcitabine, hydroxyurea, mercaptopurine, methotrexate, and thioguanine.

Examples of natural source derivatives include docetaxel, etoposide, irinotecan, taxanes (e.g. paclitaxel), teniposide, topotecan, vinblastine, vincristine, vinorelbine, prednisone, and tamoxifen.

Additional examples of chemotherapeutic agents that can be used in the invention include asparaginase and mitotane.

Furthermore, also C2 ceramide can be used.

"Linked" according to the present invention is understood to encompass both covalent and non-covalent linkage, preferably covalent linkage. In the embodiment of a covalent linkage, the binding molecule of the invention may be linked directly to therapeutically active agent or diagnostic compound or via a suitable linker molecule. In a more preferred embodiment of the present invention, the binding molecule is linked to the therapeutically active agent or diagnostic compound via a linker. Suitable linkers are known in the art.

Therefore, in one preferred embodiment the binding molecule is covalently linked to a therapeutically active substance and/or the diagnostic compound, optionally via a linker.

Suitable radionuclides include $^{67/64}Cu$, $^{131}I$, $^{124}I$, or $^{90}Y$. Such radionuclides may be linked by complex-forming moieties, or, in the case of iodine, directly by covalent linkage to the binding molecule of the invention. The complex-forming moieties are preferably covalently linked to the binding molecule, optionally by a linker.

Such antibody conjugates are known in the art (Wu A M, Senter P D. Arming antibodies: prospects and challenges for immunoconjugates. Nature Biotechnol. 23:1137-1146, 2005, Pastan I, Hassan R, FitzGerald D J, Kreitman R J. Immunotoxin treatment of cancer. Annu. Rev. Med. 58:221-237, 2007, WO 90/12592, WO 2007/030642, WO 2004/067038, WO 2004/003183, US 2005/0074426, WO 94/04189).

In a more preferred embodiment, the therapeutically active substance is a chemotherapeutic compound, or a cytotoxic compound or a cytostatic compound selected from a DNA damaging agent, in particular actinomycin-D, mitomycin C, cisplatin, doxorubicin, etoposide, verapamil, podophyllotoxin, 5-FU, a natural source derivative, and a taxan, preferably paclitaxel and carboplatin.

Further, it may be advantageous to link the binding molecules of the invention to a diagnostic compound.

A diagnostic compound is a compound which is capable of producing a signal via direct or indirect detection. In one preferred embodiment, the compound is suitable for administration to an animal, such as a mammal, more preferably human. In this embodiment, the linked binding molecule may be suitable both for in vitro and in vivo use. In another preferred embodiment, the compound is not suitable for administration to an animal, such as a mammal, more preferably human. In this embodiment, the linked binding molecule may be suitable for in vitro use. The diagnostic compound thus may be detected directly or indirectly. For direct detection, the diagnostic compounds suitable for use in the present invention can be selected from any known detectable marker groups, like chromogens, fluorescent groups, chemiluminescent groups (e.g. acridinium esters or dioxetanes), electrochemiluminescent compounds, catalysts, enzymes, enzymatic substrates, dyes, fluorescent dyes (e.g. fluorescein, coumarin, rhodamine, oxazine, resorufin, cyanine and derivatives thereof), colloidal metallic and nonmetallic particles, and organic polymer latex particles. Other examples of diagnostic compounds are luminescent metal complexes, such as ruthenium or europium complexes and radioisotopes.

Indirect detection systems comprise, for example, partners of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone.

Therefore, in a further embodiment, the invention relates to a binding molecule of the invention linked to a diagnostic compound, preferably selected from a radionuclide, a chemiluminescent compound, a fluorescent compound, a dye or an enzyme.

As shown in the Examples, the L1-OV52.24 monoclonal antibody was successfully linked to a fluorescent compound or fluorescent dye, namely to an Alexa dye (Alexa488).

In another embodiment, the present invention relates to a hybridoma cell that produces an anti-L1 monoclonal antibody of the invention.

In another embodiment, the present invention relates to a nucleic acid
(i) coding for a binding molecule according to the invention, and/or
(ii) encoding at least one chain of a binding molecule according to the invention, and/or
(iii) comprising the sequence according to SEQ ID No: 3 and/or according to SEQ ID No: 4, and/or
(iv) comprising sequence(s) encoding at least one of the sequences KASQNVGTNVA (SEQ ID No: 5), STSYRYS (SEQ ID No: 6), QQYNTYPYT (SEQ ID No: 7), FNIKDYYMQ (SEQ ID No: 8), WIDPENGKTVFDPK-FRG (SEQ ID No: 9), and WNPLAF (SEQ ID No: 10).

In a more preferred embodiment, the nucleic acid of the invention is part of a vector. Such vector is preferably a vector for expression in bacteria, such as E. coli, in a yeast cell, in insect cells or mammalian cells. Preferably, the nucleic acids of the invention are under the control of suitable regulatory sequences such as promotors or enhancers in the vector, thereby allowing expression in a host cell. The vectors preferably comprise sequences enabling replication in a host cell.

Preferably, the binding molecule linked to a diagnostic compound may be used for diagnostic purposes in vitro and thereby relates to an important tool for biotechnological research. For example, biopsies of patients or bodily samples in general may be analyzed using the binding molecules of the invention. Therefore, a further embodiment, the present invention relates to the use of a binding molecule of the invention as an in vitro diagnostic agent or as an in vitro biotechnological agent. In a more preferred embodiment, the present invention relates to the use of a binding molecule of the invention linked to a diagnostic compound as an in vitro diagnostic agent or as an in vitro biotechnological agent. In another preferred embodiment, the present invention relates to the use of a binding molecule of the invention linked to a therapeutically active substance as an in vitro biotechnological agent.

In a yet further embodiment, the present invention relates to a binding molecule of the invention, for use as a medicament or diagnostic agent.

In a particularly preferred embodiment, the binding molecule for use as a medicament is a binding molecule linked to a therapeutically active substance, as described above. The binding molecule delivers the therapeutically active substance into a tumor cell where the binding molecule linked to a therapeutically active substance can exert its therapeutic effect.

In a preferred embodiment, the therapeutically active substance is administered in a therapeutically effective amount.

In a further preferred embodiment, the binding molecule for use as a diagnostic is a binding molecule linked to a diagnostic compound. Thereby, imaging can be performed with the patient, thereby allowing diagnosis, such as prognosis or monitoring of therapy with a binding molecule of the invention. Therefore, the binding molecule of the invention linked to a diagnostic compound is preferably a companion diagnostic for the binding molecule linked to a therapeutically active substance of the invention.

The binding molecules of the invention are preferably included in a pharmaceutical composition.

It is possible that a compound is both a diagnostic compound and a therapeutically active substance. An example are certain radionuclides, such as $^{131}$I, which may be suitable both for imaging in vivo and for therapy of tumors.

In general, the pharmaceutical compositions of the present invention comprise a therapeutically effective amount of a binding molecule of the invention, an optionally one or more pharmaceutically acceptable carriers. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc.

The amount of the therapeutic of the invention, which will be effective in the treatment of a particular disorder or condition, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems. In general, suppositories may contain active ingredient in the range of 0.5% to 10% by weight; oral formulations preferably contain 10% to 95% active ingredient.

Various delivery systems are known and can be used to administer a therapeutic of the invention, e.g., encapsulation in liposomes, microparticles, and microcapsules: use of recombinant cells capable of expressing the therapeutic, use of receptor-mediated endocytosis (e.g., Wu and Wu, 1987, J. Biol. Chem. 262:4429-4432); construction of a therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion, by bolus injection, by absorption through epithelial or mucocutaneous linings (e.g., oral, rectal and intestinal mucosa, etc.), and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the therapeutic can be delivered in a vesicle, in particular a liposome (Langer, 1990, Science 249:1527-1533), more particular a cationic liposome (WO 98/40052).

In yet another embodiment, the therapeutic can be delivered via a controlled release system. In one embodiment, a pump may be used (Langer, supra). In yet another embodiment, a controlled release system can be placed in proximity of the therapeutic target, thus requiring only a fraction of the systemic dose.

Within the context of this aspect of the invention, the invention also includes a method for treating or preventing a tumor disease in a patient, comprising administering to said patient a therapeutically effective amount of binding molecule, preferably monoclonal antibody or antigen-binding fragment thereof, of the invention.

Throughout the invention, the term "effective amount" means that a given molecule or compound is administered in an amount sufficient to obtain a desired therapeutic effect. In case that, throughout the invention, two compounds are administered in a therapeutic effective amount, this includes that one or each of the compounds is administered in a subtherapeutic amount, i.e. that the amount of each compound on its own is not sufficient to provide a therapeutic effect, but that the combination of the compounds results in the desired therapeutic effect. However, it is also included within the present invention that each of the compounds on its own is administered in a therapeutically effective amount.

According to the invention, the term "treatment of tumor disease" includes both the killing of tumor cells, the reduction of the proliferation of tumor cells (e.g. by at least 30%, at least 50% or at least 90%) as well as the complete inhibition of the proliferation of tumor cells in a patient suffering from a tumor disease. In addition, this term includes the prevention of a tumorigenic disease, e.g. by killing of cells that may or a prone to become a tumor cell in the future as well as the formation of metastases.

According to the invention, the skilled person will understand that the individual therapy to be applied will depend on the e.g. physical conditions of the patient or on the severity of the disease and will therefore have to be adjusted on a case to case basis.

The invention also relates to pharmaceutical compositions comprising the monoclonal antibody or antigen-binding fragment thereof or binding molecule of the invention. With respect to said pharmaceutical composition, all embodiments described above also apply.

In a yet further embodiment, the present invention relates to a binding molecule of the invention, preferably monoclonal antibody or antigen-binding fragment thereof, for use in treating or preventing a tumor disease, preferably wherein the tumor disease is an epithelial tumor disease and/or is selected from the group consisting of astrocytoma, oligodendroglioma, meningioma, neurofibroma, glioblastoma, ependymoma, Schwannoma, neurofibrosarcoma, medulloblastoma, melanoma, pancreatic cancer, prostate carcinoma, head and neck cancer, breast cancer, lung cancer, ovarian cancer, endometrial cancer, renal cancer, neuroblastoma, squamous carcinoma, medulloblastoma, hepatoma, colon cancer, mesothelioma and epidermoid carcinoma.

In a yet further embodiment, the present invention relates to a pharmaceutical composition, comprising a binding molecule of the invention and optionally one or more pharmaceutically acceptable carriers, as described above.

In another embodiment, the present invention relates to a binding molecule binding to L1, wherein the binding molecule is an anti-L1 monoclonal antibody or antigen-binding fragment thereof, characterized in that at least one of the complementarity determining regions (CDRs) of the anti-L1 monoclonal antibody or antigen-binding fragment thereof a) has one of the sequences selected from KASQNVGTNVA (SEQ ID No: 5), STSYRYS (SEQ ID No: 6), QQYNTYPYT (SEQ ID No: 7), FNIKDYYMQ (SEQ ID No: 8), WIDPENGKTVFDPKFRG (SEQ ID No: 9), and WNPLAF (SEQ ID No: 10), or b) has a sequence which, in comparison to the sequences mentioned under a) has at least one conservative amino acid exchange.

In another embodiment, the present invention relates to a binding molecule binding to L1, characterized in that the binding molecule comprises a) at least one of the sequences selected from KASQNVGT-NVA (SEQ ID No: 5), STSYRYS (SEQ ID No: 6), QQYNTYPYT (SEQ ID No: 7), FNIKDYYMQ (SEQ ID No: 8), WIDPENGKTVFDPKFRG (SEQ ID No: 9), and WNPLAF (SEQ ID No: 10), or b) comprises a sequence which, in comparison to the sequences mentioned under a) has at least one conservative amino acid exchange.

Such a monoclonal antibody or antibody-binding fragment thereof or binding molecules of the invention can, e.g. be produced by CDR grafting or by recombinant production of the antibody. Such methods are known in the art (see e.g. Queen, U.S. Pat. No. 5,585,089 and Winter, U.S. Pat. No. 5,225,539, Cabilly U.S. Pat. No. 4,816,567).

The preferred embodiments of the invention described herein apply to all binding molecules and monoclonal antibodies and antigen-binding fragments thereof of the invention.

REFERENCES

1. Galluzzi L, Vacchelli E, Fridman W H, Galon J, Sautes-Fridman C, Tartour E, Zucman-Rossi J, Zitvogel L, Kroemer G: Trial Watch: Monoclonal antibodies in cancer therapy. Oncoimmunology 2012, 1(1):28-37.
2. Presta L G: Molecular engineering and design of therapeutic antibodies. Curr Opin Immunol 2008, 20(4):460-470.
3. Reichert J M: Marketed therapeutic antibodies compendium. MAbs 2012, 4(3).
4. Reichert J M: Antibodies to watch in 2014: mid-year update. mAbs 2014, 6(4):799-802.
5. Reichert J M: Antibody-based therapeutics to watch in 2011. MAbs 2011, 3(1):76-99.
6. Wolterink S, Moldenhauer G, Fogel M, Kiefel H, Pfeifer M, Luttgau S, Gouveia R, Costa J, Endell J, Moebius U et al: Therapeutic antibodies to human L1CAM: functional characterization and application in a mouse model for ovarian carcinoma. Cancer Res 2010, 70(6):2504-2515.
7. Doberstein K, Harter P N, Haberkorn U, Bretz N P, Arnold B, Carretero R, Moldenhauer G, Mittelbronn M, Altevogt P: Antibody therapy to human L1CAM in a transgenic mouse model blocks local tumor growth but induces EMT. International journal of cancer Journal international du cancer 2014.
8. Novak-Hofer I, Amstutz H P, Morgenthaler J J, Schubiger P A: Internalization and degradation of monoclonal antibody chCE7 by human neuroblastoma cells. International journal of cancer Journal international du cancer 1994, 57(3):427-432.
9. Schaefer A W, Kamiguchi H, Wong E V, Beach C M, Landreth G, Lemmon V: Activation of the MAPK signal cascade by the neural cell adhesion molecule L1 requires L1 internalization. The Journal of biological chemistry 1999, 274(53):37965-37973.
10. Long K E, Asou H, Snider M D, Lemmon V: The role of endocytosis in regulating L1-mediated adhesion. The Journal of biological chemistry 2001, 276(2):1285-1290.
11. Schaefer A W, Kamei Y, Kamiguchi H, Wong E V, Rapoport I, Kirchhausen T, Beach C M, Landreth G, Lemmon S K, Lemmon V: L1 endocytosis is controlled by a phosphorylation-dephosphorylation cycle stimulated by outside-in signaling by L1. The Journal of cell biology 2002, 157(7):1223-1232.
12. WO 2008/151819

FIGURES

FIG. 1: Measuring cellular uptake of mAb L1CAM mAb 9.3 on Skov3ip cells.

Skov3ip cells were incubated for different length of time with Alexa488 conjugated L1CAM mAb L1-9.3. Samples were subsequently fixed and cell surface bound antibody was detected using a secondary goat-anti-mouse antibody coupled to Alexa647. Cells at time point 0' were incubated on ice to avoid antibody internalization. Samples were measured on an Amnis ISX imaging flow cytometer and 3000 cells were collected and analyzed using the Amnis IDEAS software. (A) shows a representative imagery of the acquired cells at time points 0 minutes, 60 minutes (B) and 90 minutes (C). The panel of graphs underneath shows the respective quantitation of the samples. (D) depicts time point 0', (E) 60' and 90' (F). The y-axis gives the normalized frequency and the x-axis shows the respective intracellular fluorescence intensity of the Alexa488-conjugated L1CAM mAb 9.3 in relation to total fluorescence intensity of the cell. The table under the graphs shows the number of cells included in the analysis (counts) and the mean value of the graph (mean). The experiment was repeated thrice, shown is a representative result.

Figure 2:
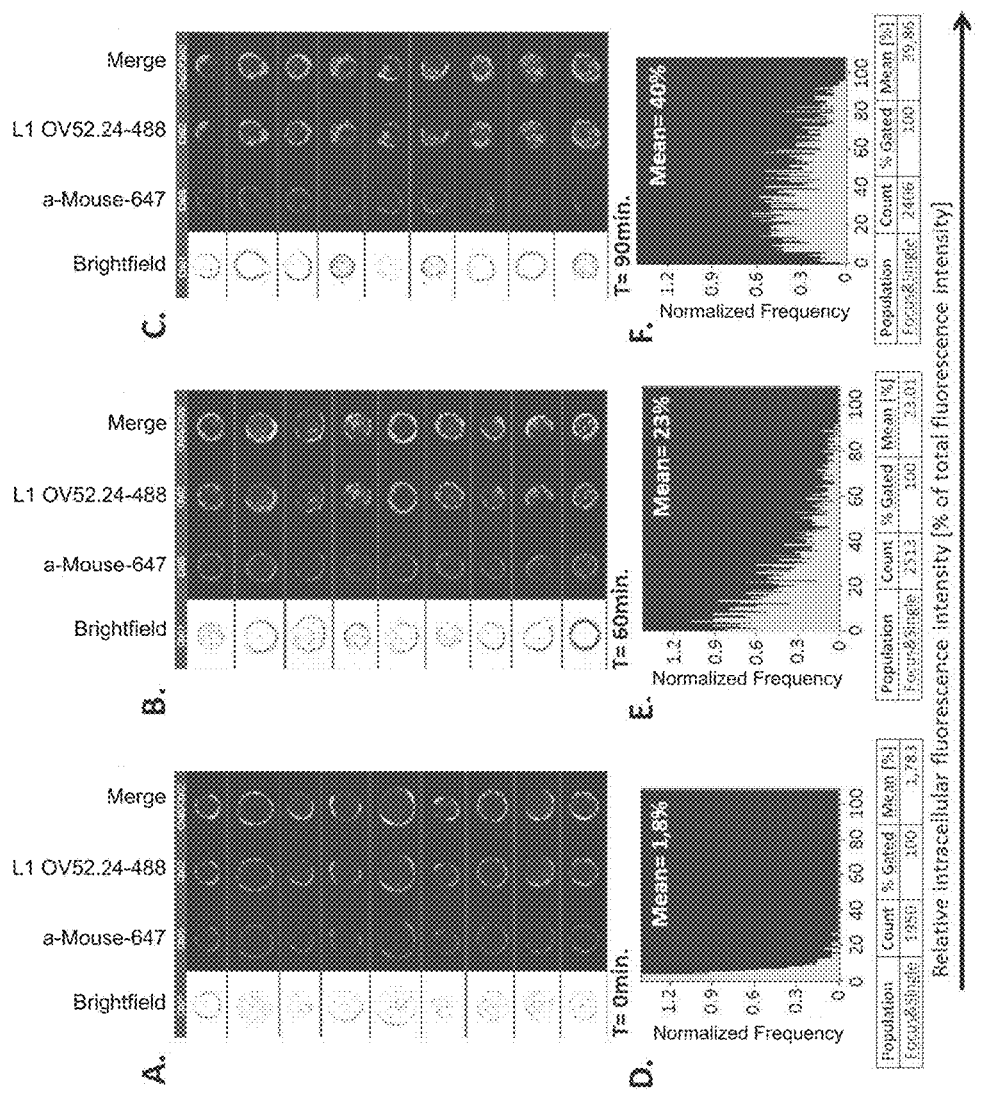

FIG. 2: Measuring cellular uptake of antibody L1CAM mAb OV52.24 on Skov3ip cells.

Skov3ip cells were incubated for different length of time with Alexa488 conjugated L1 mAb OV52.24. Samples were subsequently fixed and cell surface bound antibody was detected using a secondary goat-anti-mouse antibody coupled to Alexa647. Cells at time point 0' were incubated on ice to avoid antibody internalization. Samples were measured on an Amnis ISX imaging flow cytometer and 3000 cells were collected and analyzed using the Amnis IDEAS software. (A) shows a representative imagery of the acquired cells at time points 0 minutes, 60 minutes (B) and 90 minutes (C). The panel of graphs underneath shows the respective quantitation of the samples. (D) depicts time point 0', (E) 60' and 90' (F). The y-axis gives the normalized frequency and the x-axis shows the respective intracellular fluorescence intensity of the Alexa488-conjugated L1 mAb OV52.24 in relation to total fluorescence intensity of the cell. The table under the graphs shows the number of cells included in the analysis (count) and the mean value of the graph (mean). The experiment was repeated thrice, shown is a representative result.

Figure 3:
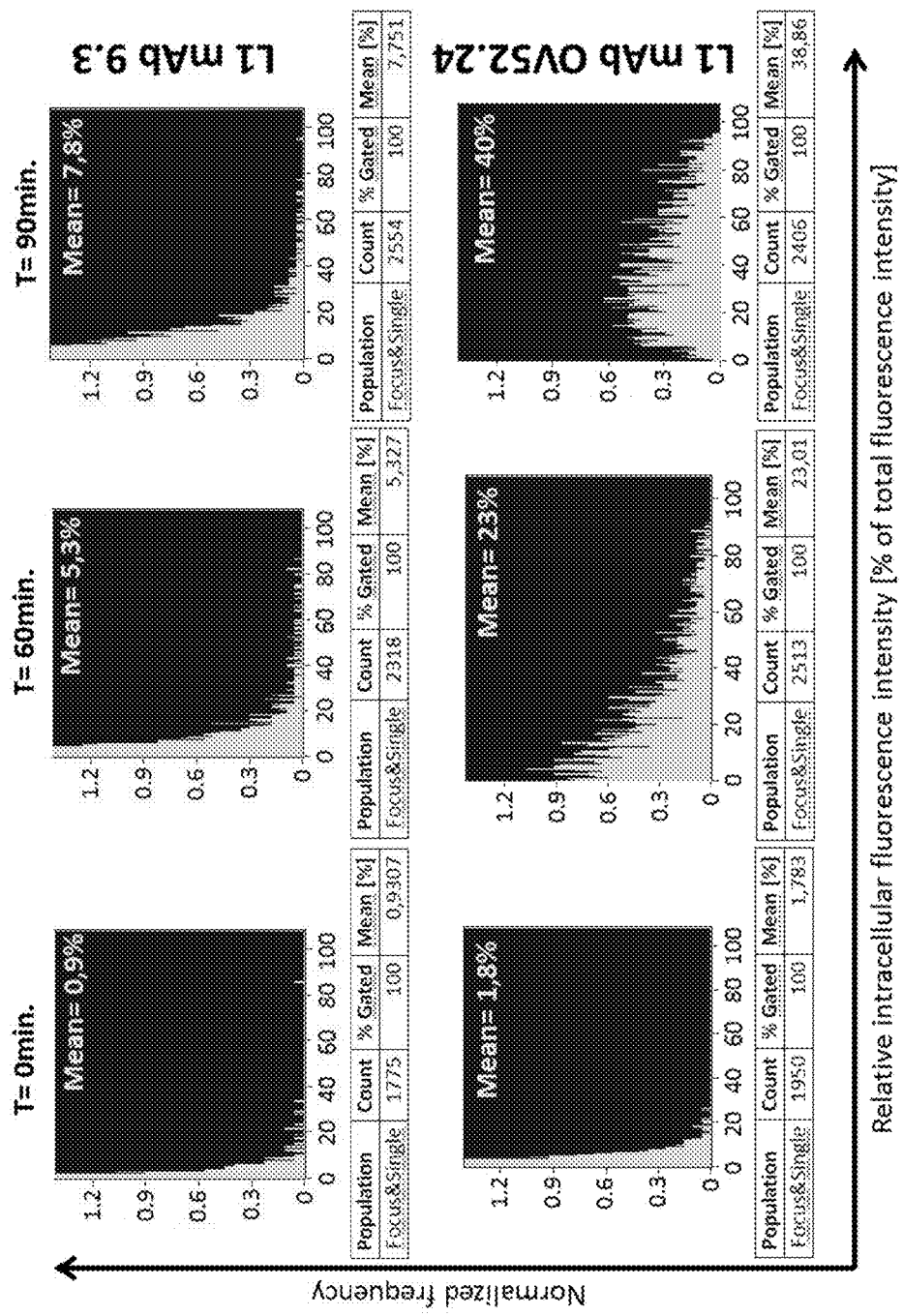

FIG. 3: Measuring cellular uptake L1CAM mAbs 9.3 and OV52.24 on Skov3ip cells.

The figure gives an overview of the results from FIG. 1 and FIG. 2. The upper panel shows the graphs for L1CAM mAb 9.3 and the lower panel for L1CAM mAb OV52.24 for the different time points 0', 60' and 90 minutes.

Figure 4:
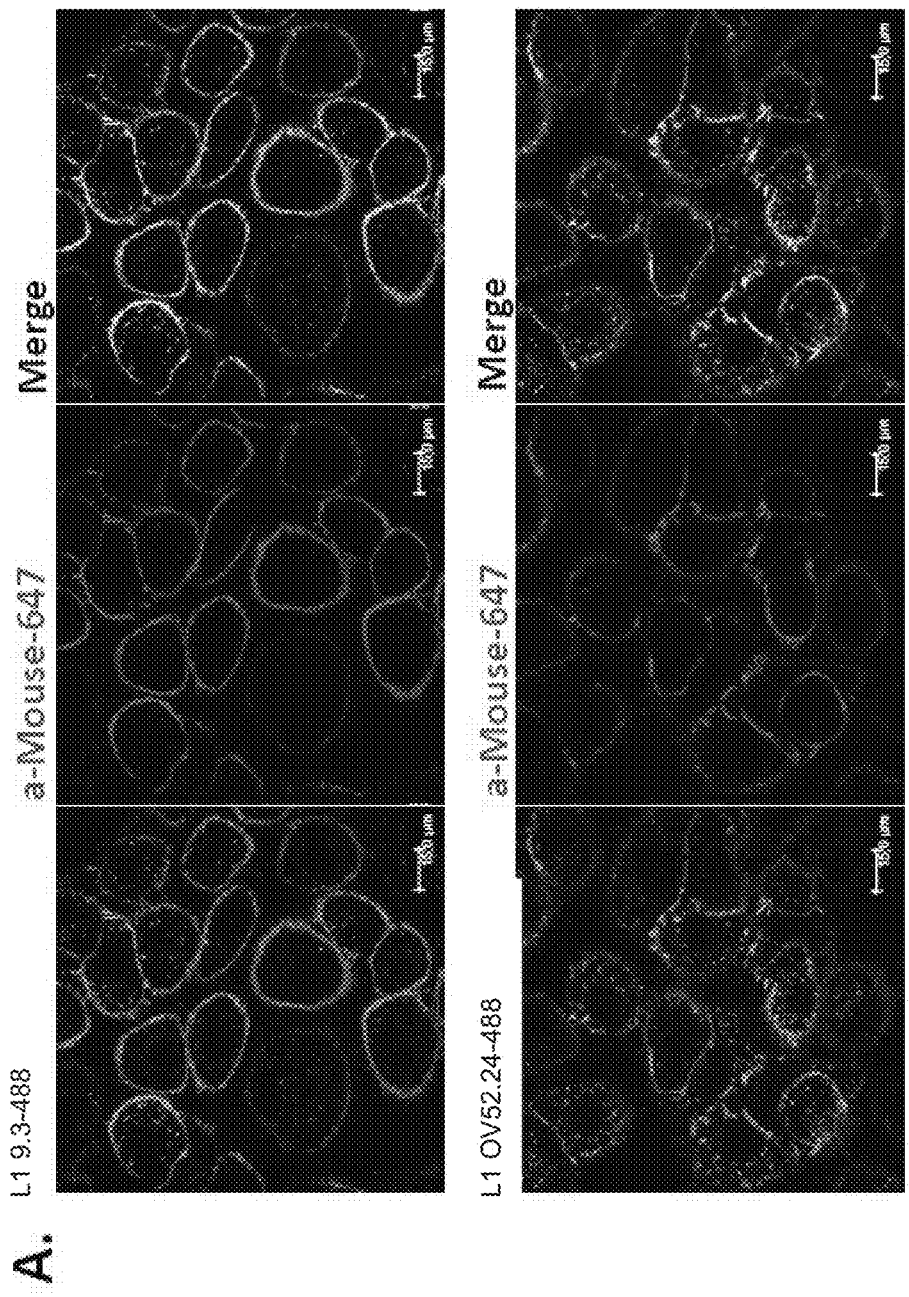
Figure 4:
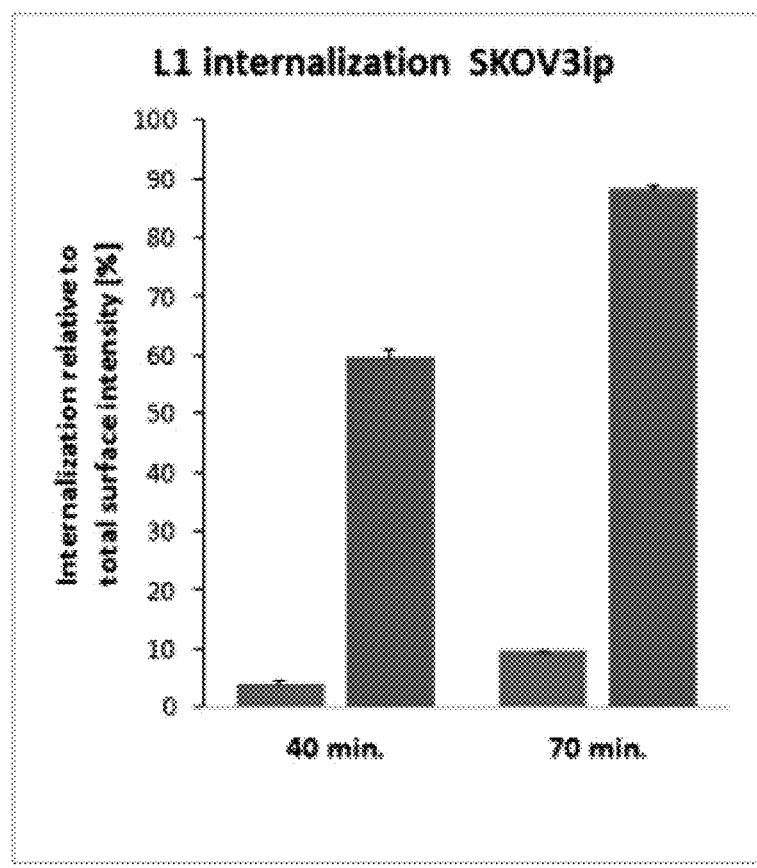

FIG. 4: Measuring cellular uptake of L1CAM mAbs 9.3 and OV52.24 on Skov3ip cells using confocal laser scanning microscopy.

Skov3ip cells were incubated for 70 minutes with Alexa488 conjugated L1CAM mAbs 9.3 or OV52.24. Samples were subsequently fixed and cell surface bound antibody was detected using a secondary goat-anti-mouse antibody coupled to Alexa647. Samples were then visualized on a Leica SP5 II confocal laser scanning microscope. Z-slices were acquired in similar z-positions. For every antibody n=30 cells were acquired and quantitated (A). Images were analyzed using Fiji (ImageJ) and plotted as a bar graph showing intracellular fluorescence intensity of the Alexa488-conjugated L1 mAb 9.3 and L1-OV52.24 in relation to total fluorescence intensity of the cell (B). The experiment was repeated thrice, shown is a representative result. The respective left bar for 40 min. and 90 min., respectively, shows the results for mAb 9.3. The respective right bar for 40 min. and 90 min., respectively, shows the results for mAb OV52.24.

Figure 5:
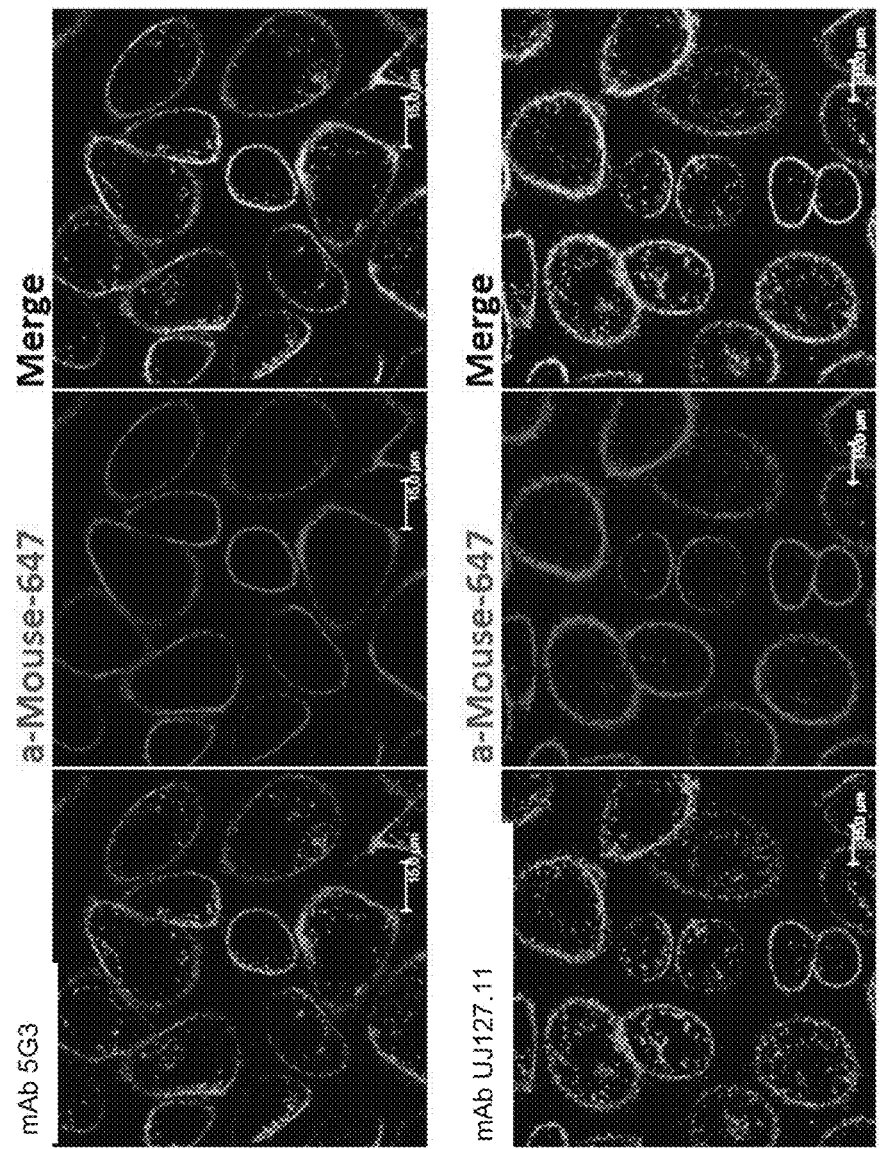

FIG. 5: Confirming cellular uptake of L1CAM mAbs 5G3 and UJ127.11 on Skov3ip cells using confocal laser scanning microscopy.

Skov3ip cells were incubated for 70 minutes with Alexa488 conjugated L1CAM mAbs 5G3 and UJ127.11. Samples were subsequently fixed and cell surface bound antibody was detected using a secondary goat-anti-mouse antibody coupled to Alexa647. Samples were then visualized on a Leica SP5 II confocal laser scanning microscope. Z-slices were acquired in similar z-positions. For every antibody n=30 cells were acquired. Shown is a representative result.

FIG. 6: Measuring and comparing cellular uptake of antibody L1CAM mAbs 9.3, OV52.24, 5G3 and UJ127.11 on Skov3ip cells.

Skov3ip cells were incubated for different length of time with Alexa488 conjugated L1 mAbs. Samples were subsequently fixed and cell surface bound antibody was detected using a secondary goat-anti-mouse antibody coupled to Alexa647. Cells at time point 0' were incubated on ice to avoid antibody internalization. Samples were measured on an Amnis ISX imaging flow cytometer and 5000 cells were collected and analyzed using the Amnis IDEAS software. The left panel of graphs show time point 0 minutes, middle panel 60 minutes and right panel 90 minutes, respectively. The y-axis gives the normalized frequency and the x-axis shows the respective intracellular fluorescence intensity of the Alexa488-conjugated L1 mab in relation to total fluorescence intensity of the cell. The mean value of the relative intracellular fluorescence intensity for every condition is given in the graph. The experiment was repeated thrice, shown is a representative result.

Figure 7:
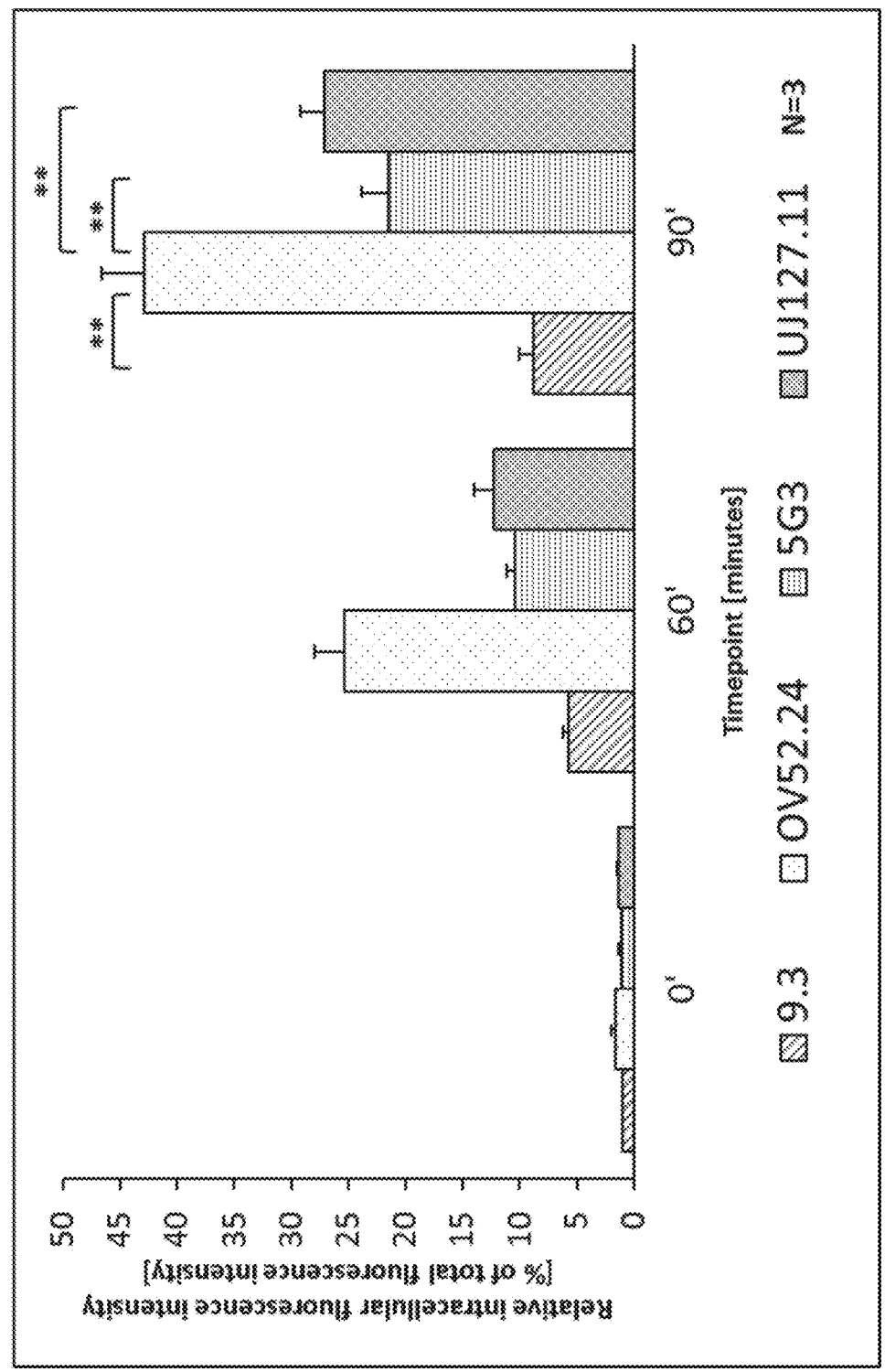

FIG. 7: Comparing cellular uptake of L1CAM mAbs 9.3, OV52.24, 5G3 and UJ127.11 on Skov3ip cells.

The figure gives a summary of the representative analysis of FIG. 6. Three different independent experiments were plotted based on the mean relative intracellular intensity of each experiment for each L1CAM mAb. Values are expressed for bar graphs as mean±S.D. To determine the probability of statistically significant increases or decreases in internalization of different L1CAM mAbs, three independent experiments were analyzed using a two-tailed, unpaired Student's t-tests. A p-value<0.05 was considered statistically significant. Asterisks were assigned as follows: *$p \leq 0.05$; $p \leq 0.01$; *$P \leq 0.001$.

EXAMPLES

Example 1

Materials and Methods

Cell Lines

Human ovarian carcinoma cells SKOV3ip were obtained from the American Type Culture Collection (Manassas, Va.). The cell lines were authenticated by the German Resource Center for Biological Material (Braunschweig, Germany) and throughout the culture by assessment of typical morphology by the investigators. Mycoplasma-negative cultures were ensured by weekly tests. Cells were cultured in DMEM medium (Sigma-Aldrich, Deisenhoffen, Germany) supplemented with 10% heat-inactivated fetal calf serum (FCS) (Biochrom, Berlin, Germany), 2 mM L-glutamine (Invitrogen, Karlsruhe, Germany) and 1 mM sodium pyruvate (Invitrogen). All cells were maintained in a humidified atmosphere at 37° C. and 5% $CO_2$.

Monoclonal Antibodies mAb L1-9.3 against human L1CAM has been described before [6, 12].

L1-OV52.24 was generated by immunization of mice with human L1-Fc protein comprising the ectodomain of L1 or using SKOV3ip cells for immunization.

The cDNA sequence of the immunoglobulin genes of the L1-OV52.24 monoclonal antibody was determined and is shown above (light chain: SEQ ID No: 3 and heavy chain: SEQ ID No: 4).

Moreover, the protein sequence of the heavy and light chain (VDJ or VJ domain, without constant domain), respectively, of L1-OV52.24 was determined (SEQ ID No: 2 and SEQ ID No: 1). Moreover, the CDR sequences of L1-OV52.24 according to the Kabat nomenclature were determined. The CDR Sequences of L1-OV52.24 are: KASQNVGTNVA (LCDR1; SEQ ID No: 5), STSYRYS (LCDR2; SEQ ID No: 6), QQYNTYPYT (LCDR3; SEQ ID No: 7), FNIKDYYMQ (HCDR1; SEQ ID No: 8), WIDPENGKTVFDPKFRG (HCDR2; SEQ ID No: 9), and WNPLAF (HCDR3; SEQ ID No: 10).

Both mAbs are of the IgG1 isotype.

An Isotype control mAb was obtained from Bio X Cell (West Lebanon, N.H.). L1CAM mAbs were conjugated to Alexa488 using a labeling kit (Invitrogen) according to manufacturer's instructions. Briefly, 100 μg of antibody were mixed with one vial of labeling reagent, incubated for one hour and subsequently purified on a column. The degree of labeling was determined to ensure similar labeling efficacy.

Binding Constants

Surface Plasmon Resonance (SPR) Equilibrium Analysis

The binding analysis was performed using a BIAcore 3000 equipped with a CM5 sensor chip. Briefly, a BIAcore CM5 chip was activated with EDC/NHS and various levels of L1-Fc were captured onto the activated surface. The remaining active sites were blocked by ethanolamine/HCl. L1-mAb were bound to the L1-Fc surface and allowed to dissociate over time. The association and dissociation phases for each injection over each density surface were subjected to kinetic analysis.

Epitope Recognized

To determine the epitope specificity, we constructed a series of L1-Fc proteins carrying distinct Ig domains (as described in [6]). For fine mapping recombinant V5-tagged L1 fragments that were described recently were used (Gouveia R M, Morais V A, Peixoto C, et al. Production and purification of functional truncated soluble forms of human recombinant L1 cell adhesion glycoprotein from Spodoptera frugiperda Sf9 cells. Protein Expr Purif 2007; 52:182-93). The recombinant proteins were used in ELISA or in Western blot analysis for epitope mapping.

Antibody Uptake Assays

For Imaging Flow Cytometry (Imagestream)

Skov3ip cells were detached with trypsin/EDTA, resuspended in culture medium, counted and divided into aliquots of equal cell number (200,000 cells). Cells were incubated at 37° C. for different time points in the continuous presence of the labeled antibody (10 µg/mL) or on ice for time point 0 minutes. At each time point cells were sedimented at 800×g, washed once with ice-cold PBS and fixed with 4% PFA (Thermo Fischer) for 15 min. on ice. Fixed cells were washed twice with PBS and incubated with a secondary goat-anti-mouse-Alexa-647 antibody at 25 µg/mL (Invitrogen, Karlsruhe, Germany) for 20 minutes and subsequently washed twice with PBS.

For Confocal Laser Scanning Microscopy 25,000 cells were seeded and grown on 8-well µ-slides (Ibidi, Munich, Germany) for 24 h. Cells were incubated at 37° C. for different time points in the continuous presence of the labeled antibody (10 µg/mL). At each time point cells were washed once with ice-cold PBS and fixed with 4% PFA (Thermo Fischer) for 15 min. on ice. Fixed cells were washed twice with PBS and incubated with a secondary goat-anti-mouse-Alexa-647 antibody at 25 µg/mL (Invitrogen, Karlsruhe, Germany) for 20 minutes and subsequently washed twice with PBS.

Imaging Flow Cytometry and Analysis

Samples were measured on an Amnis ImageStreamX (ISX) (Amnis Corp., Seattle, USA) with a 488 nm laser set to 100% and the 561 nm laser set to 80% with the 60× objective and the extended depth of field (EDF) option activated. Channel 2 and 5 as well as brightfield imagery in channel 1 were recorded and 4000 cells were collected per sample. Aliquots of cells for each antibody were taken after fixation and before counter staining with the anti-mouse-Alexa647 antibody as compensation controls for the Alexa488-coupled L1CAM mAbs. Cells were stained on ice with the respective unconjugated L1 mAbs at the same concentration as the conjugated antibodies and counter stained with the same anti-mouse-Alexa647 secondary antibody to serve as a compensation control for counter staining with the anti-mouse-Alexa647 antibody. Compensation controls were acquired with the respective compensation settings on the ISX.

Analysis of the ISX data was made with the IDEAS software (Amnis Corp., Seattle, USA). Raw image files were opened and a compensation matrix was generated using the respective compensation files. Acquired cells were gated for cells in focus and subsequently for single cells using the brightfield imagery to control the gating. A "cell-surface mask" was generated using the imagery of channel 5 whereas the intensity was limited to a lower limit of 200 and the upper limit remained unchanged at 4095 in order to eliminate background and to optimize the signal. For channel 2 the cut-off for the lower intensity was set to 150 and the upper limit remained unchanged at 4095 and termed "channel 2". Both settings were derived from control staining with the isotype control for the L1CAM mAbs or the secondary antibody alone. Additionally the "cell surface mask" was dilated by one pixel to include neighboring pixels on channel 2. Another mask termed "intracellular signal" was generated which was defined as "channel 2 and not cell-surface mask". Finally, a combined feature named "relative intracellular intensity" was generated with the following definition "intracellular signal/(Intensity_MC_Ch02*100). The respective histogram was plotted and the mean value was determined. The same procedure was applied to all samples measured.

Confocal Laser Scanning Microscopy and Analysis

Samples were measured on a Leica SP5 II (Leica microsystems, Wetzlar, Germany) confocal laser scanning microscope equipped with HyD detectors. Alexa-488 conjugated L1 mAbs were excited using an Argon laser at 488 nm and a HeNe laser line at 633 nm was used to excite Alexa-647. Z-slices were acquired in similar z-positions. For every antibody n=30 cells were acquired and quantitated. Images were analyzed using Fiji (ImageJ, NIH, Bethesda, USA) where the signal of the cell surface counter-staining with the a-mouse-Alexa-647 was used to segment and identify the boundaries of single cells and intracellular fluorescence intensity and total cellular intensity was then determined. Results were plotted as a bar graph showing intracellular fluorescence intensity of the Alexa488-conjugated mAb L1-9.3 and L1-OV52.24 in relation to total fluorescence intensity of the cell using Excel (Microsoft, Redmond, USA).

Results mAbs L1-9.3 and L1-OV52-54 bind to distinct cell surface epitopes of the L1CAM cell surface molecule. mAb 9.3 clearly reacts with a fusion protein consisting of the first Ig domain (1.Ig-L1-Fc; [12]). By Western blot analysis, it was confirmed that mAb L1-OV52.24 recognizes the 4-5FNIII domain of L1. MAb L1-9.3 binds to the first Ig-domain whereas L1-OV52.24 binds to an epitope in the 4-5. FNIII domain. mAb 9.3 has an affinity to L1 of KD (M)=$8.5*10^{-11}$ [see [6]], whereas mAb L1-OV52.24 has an affinity to L1 of KD (M)=$2.41*10^{-9}$. L1-OV52.24 was found to perform excellently in Western Blot Analysis and FACS analysis experiments and was found to perform well in immunohistochemistry (IHC) experiments.

We carried out internalization assays in SKOV3ip cells using Alex-488 conjugated mAbs as outlined in the material & method section above. Internalization was measured by Imagestream$^X$ analysis that combines FACS and fluorescent analysis and allows the quantification of thousands of cells. Data were analyzed with the IDEAS software. Analysis of L1-9.3 showed slow internalization at timepoints 0 min, 60 min and 90 min (FIG. 1 A-F) with a mean of 7.8% at the final timepoint. In contrast, the mAb L1-OV52.24 internalized much faster and reached a mean value of 40% at the final timepoint (FIG. 2 A-F). The data are directly compared in FIG. 3.

To verify these results were carried out a similar analysis with attached cells. SKOV3ip cells were grown on coverslips and allowed to internalize with Alexa-conjugated antibodies. The quantification was done by laser scanning microscopy and visual counting of cells. Staining examples are shown in FIG. 4A and the results are summarized in FIG. 4B. These results confirm the data obtained by Imagestream analysis and show that the mAb L1-OV52.24 induces a close to tenfold higher internalization rate. The results are unexpected and suggest that mAb-L1-OV52.24 is suitable for delivery of antibody-drug conjugates.

Example 2

Materials and Methods

Cell Lines

Human ovarian carcinoma cells SKOV3ip were obtained from the American Type Culture Collection (Manassas, Va.). The cell lines were authenticated by the German Resource Center for Biological Material (Braunschweig, Germany) and throughout the culture by assessment of typical morphology by the investigators. Mycoplasma-negative cultures were ensured by weekly tests. Cells were cultured in DMEM medium (Sigma-Aldrich, Deisenhoffen, Germany) supplemented with 10% heat-inactivated fetal calf serum (FCS) (Biochrom, Berlin, Germany), 2 mM L-glutamine (Invitrogen, Karlsruhe, Germany) and 1 mM sodium pyruvate (Invitrogen). All cells were maintained in a humidified atmosphere at 37° C. and 5% $CO_2$.

Monoclonal Antibodies

The mAbs L1-9.3, 5G3 and UJ127.11 against human L1CAM have been described before [6].

L1-OV52.24 was generated by immunization of mice with human L1-Fc protein comprising the ectodomain of L1 or using SKOV3ip cells for immunization.

The cDNA sequence of the immunoglobulin genes of the L1-OV52.24 monoclonal antibody was determined and is shown above (light chain: SEQ ID No: 3 and heavy chain: SEQ ID No: 4).

Moreover, the protein sequence of the heavy and light chain (VDJ or VJ domain, without constant domain), respectively, of L1-OV52.24 was determined (SEQ ID No: 2 and SEQ ID No: 1). Moreover, the CDR sequences of L1-OV52.24 according to the Kabat nomenclature were determined. The CDR Sequences of L1-OV52.24 are: KASQNVGTNVA (LCDR1; SEQ ID No: 5), STSYRYS (LCDR2; SEQ ID No: 6), QQYNTYPYT (LCDR3; SEQ ID No: 7), FNIKDYYMQ (HCDR1; SEQ ID No: 8), WIDPENGKTVFDPKFRG (HCDR2; SEQ ID No: 9), and WNPLAF (HCDR3; SEQ ID No: 10).

mAbs L1-9.3, L1-OV52.24 and UJ127.11 are of the IgG1 isotype. mAb 5G3 is of the IgG2a isotype. Corresponding Isotype control mAbs were obtained from Bio X Cell (West Lebanon, N.H.). L1CAM mAbs were conjugated to Alexa488 using a labeling kit (Invitrogen) according to manufacturer's instructions. Briefly, 100 μg of antibody were mixed with one vial of labeling reagent, incubated for one hour and subsequently purified on a column. The degree of labeling was determined to ensure similar labeling efficacy. mAb 5G3 conjugated to Alexa488 was purchased from Novus Biologicals (Littleton, USA).

Antibody Uptake Assays

For Imaging Flow Cytometry (Imagestream)

Skov3ip cells were detached with trypsin/EDTA, resuspended in culture medium, counted and divided into aliquots of equal cell number (200,000 cells). Cells were incubated at 37° C. for different time points in the continuous presence of the labeled antibody (10 μg/mL) or on ice for time point 0 minutes. At each time point cells were sedimented at 800×g, washed once with ice-cold PBS and fixed with 4% PFA (Thermo Fischer) for 15 min. on ice. Fixed cells were washed twice with PBS and incubated with a secondary goat-anti-mouse-Alexa-647 antibody at 25 μg/mL (Invitrogen, Karlsruhe, Germany) for 20 minutes and subsequently washed twice with PBS.

For Confocal Laser Scanning Microscopy 25,000 cells were seeded and grown on 8-well μ-slides (Ibidi, Munich, Germany) for 24 h. Cells were incubated at 37° C. for different time points in the continuous presence of the labeled antibody (10 μg/mL). At each time point cells were washed once with ice-cold PBS and fixed with 4% PFA (Thermo Fischer) for 15 min. on ice. Fixed cells were washed twice with PBS and incubated with a secondary goat-anti-mouse-Alexa-647 antibody at 25 μg/mL (Invitrogen, Karlsruhe, Germany) for 20 minutes and subsequently washed twice with PBS.

Imaging Flow Cytometry and Analysis

Samples were measured on an Amnis ImageStreamX (ISX) (Amnis Corp., Seattle, USA) with a 488 nm laser set to 100% and the 561 nm laser set to 80% with the 60× objective and the extended depth of field (EDF) option activated. Channel 2 and 5 as well as brightfield imagery in channel 1 were recorded and 10.000 cells were collected per sample. Aliquots of cells for each antibody were taken after fixation and before counter staining with the anti-mouse-Alexa647 antibody as compensation controls for the Alexa488-coupled L1 mAbs. Cells were stained on ice with the respective unconjugated L1 mAbs at the same concentration as the conjugated antibodies and counter stained with the same anti-mouse-Alexa647 secondary antibody to serve as a compensation control for counter staining with the anti-mouse-Alexa647 antibody. Compensation controls were acquired with the respective compensation settings on the ISX.

Analysis of the ISX data was made with the IDEAS software (Amnis Corp., Seattle, USA). Raw image files were opened and a compensation matrix was generated using the respective compensation files. Acquired cells were gated for cells in focus and subsequently for single cells using the brightfield imagery to control the gating. A "cell-surface mask" was generated using the imagery of channel 5 whereas the intensity was limited to a lower limit of 200 and the upper limit remained unchanged at 4095 in order to eliminate background and to optimize the signal. For channel 2 the cut-off for the lower intensity was set to 150 and the upper limit remained unchanged at 4095 and termed "channel 2". Both settings were derived from control staining with the isotype control for the L1 mAbs or the secondary antibody alone. Additionally the "cell surface mask" was dilated by one pixel to include neighboring pixels on channel 2. Another mask termed "intracellular signal" was generated which was defined as "channel 2 and not cell-surface mask". Finally, a combined feature named "relative intracellular intensity" was generated with the following definition "intracellular signal/(Intensity_MC_Ch02*100). The respective histogram was plotted and the mean value was determined. The same procedure was applied to all samples measured.

Confocal Laser Scanning Microscopy

Samples were measured on a Leica SP5 II (Leica microsystems, Wetzlar, Germany) confocal laser scanning microscope equipped with HyD detectors. Alexa-488 conjugated L1 mAbs were excited using an Argon laser at 488 nm and a HeNe laser line at 633 nm was used to excite Alexa-647. Z-slices were acquired in similar z-positions. For every antibody n=30 cells were acquired. Representative images are shown.

Statistics

The probability of statistically significant increases or decreases between conditions of at least three independent experiments was determined using the Student's t-test. Two-tailed, unpaired t-tests were performed. Values are expressed for bar graphs as mean±S.D. A p-value<0.05 was considered statistically significant. Significance in graphs was illustrated by using asterisks. Asterisks were assigned as follows: *p≤05; p≤0.01; *p≤0.001.

Results

The results of Example 2 are shown in FIGS. 5 to 7. We carried out internalization assays in SKOV3ip cells using Alex-488 conjugated mAbs as outlined in the material & method section above. Internalization was measured by Imagestream$^X$ analysis that combines FACS and fluorescent analysis and allows the quantification of thousands of cells.

Data were analyzed with the IDEAS software. Analysis showed slow internalization at timepoints 0 min, 60 min and 90 min for monoclonal antibodies L1-9.3, 5G3 and UJ127.11 of the prior art (FIG. 6). In contrast, mAb L1-OV52.24 of the present invention internalized much faster and reached a mean value of 41.7% at the final timepoint (FIG. 6). The data are summarized in FIG. 7. It was surprisingly found that the internalization of L1-OV52.24 at 90' is statistically higher than the internalization of any of the prior art anti-L1 monoclonal antibodies 9.3, 5G3 and UJ127.11, with a p-value≤0.01, respectively.

To verify these results, a similar analysis was carried out with attached cells. SKOV3ip cells were grown on coverslips and allowed to internalize with Alexa-conjugated antibodies. The quantification was done by laser scanning microscopy and visual counting of cells. Staining examples are shown in FIG. 5. These results confirm the data obtained by Imagestream analysis and show that the mAb L1-OV52.24 induces a surprisingly high internalization rate as compared to the prior art antibodies directed against L1CAM. The results are unexpected and suggest that mAb-L1-OV52.24 is suitable for delivery of antibody-drug conjugates.

The invention claimed is:

1. A binding molecule binding to L1CAM (L1 cell adhesion molecule), wherein
the binding molecule is an anti-L1 CAM monoclonal antibody or an antigen-binding fragment thereof, or
the binding molecule is selected from the group consisting of a single chain antibody, an antigen-binding fragment of an antibody, and a bispecific antibody, or
the binding molecule is a chimeric antibody, a humanized antibody, or an antigen-binding fragment thereof,
characterized in that the binding molecule comprises the complementarity determining regions (CDRs) KASQNVGTNVA (SEQ ID No: 5), STSYRYS (SEQ ID No: 6), QQYNTYPYT (SEQ ID No: 7), FNIKDYYMQ (SEQ ID No: 8), WIDPENGKTVFDPKFRG (SEQ ID No: 9), and WNPLAF (SEQ ID No: 10).

2. The binding molecule of claim 1, wherein the binding molecule is an anti-L1CAM monoclonal antibody or an antigen-binding fragment thereof.

3. The binding molecule of claim 1,
wherein the binding molecule is selected from the group consisting of a single chain antibody, an antigen binding fragment of an antibody, and a bispecific antibody, or
wherein the binding molecule is a chimeric antibody, a humanized antibody, or an antigen-binding fragment thereof.

4. The binding molecule of claim 1,
(i) which binds L1CAM with an affinity (KD) of at least $10^{-9}$ M, or
(ii) which is internalized by a mammalian cell expressing L1CAM.

5. The binding molecule of claim 1, which is the monoclonal antibody L1-OV52.24 or an antigen-binding fragment thereof,
wherein the variable part of the light chain of L1-OV52.24 comprises the sequence of SEQ ID No: 1 or wherein the light chain is encoded by SEQ ID No: 3, and wherein the variable part of the heavy chain of L1-OV52.24 comprises the sequence of SEQ ID No: 2 or wherein the heavy chain is encoded by SEQ ID No: 4.

6. The binding molecule of claim 1,
(a) linked to a therapeutically active substance, and/or
(b) linked to a diagnostic compound.

7. A pharmaceutical composition, comprising a binding molecule of claim 1 and one or more pharmaceutically acceptable carriers.

8. The binding molecule of claim 1, wherein said single chain antibody is selected from an scFv and a multimer of scFv.

9. The binding molecule of claim 8, wherein said multimer of scFv is a diabody, triabody or tetrabody.

10. The binding molecule of claim 1, wherein said antigen-binding fragment is a Fab.

11. The binding molecule of claim 6, wherein said therapeutically active substance is a chemotherapeutic compound, a cytotoxic compound, a cytostatic compound, a cytokine, a nanoparticle, or a radionuclide.

12. The binding molecule of claim 11, wherein said chemotherapeutic compound is an alkylating agent, antineoplastic antibiotic, or an antimetabolite.

13. The binding molecule of claim 6, wherein said diagnostic compound is a radionuclide, a chemiluminescent compound, a fluorescent compound, a dye or an enzyme.

14. The binding molecule of claim 11, wherein said therapeutically active substance is a chemotherapeutic compound or a cytotoxic compound or a cytostatic compound.

15. The binding molecule of claim 14, wherein said chemotherapeutic compound or cytotoxic compound or cytostatic compound is a DNA damaging agent or a taxan.

16. The binding molecule of claim 15, wherein said DNA damaging agent is actinomycin-D, mitomycin C, cisplatin, doxorubicin, etoposide, verapamil, podophyllotoxin or 5-FU.

17. The binding molecule of claim 15, wherein said taxan is paclitaxel or carboplatin.

18. The binding molecule of claim 6, wherein said binding molecule is covalently linked to said therapeutically active substance or said diagnostic compound.

19. The binding molecule of claim 18, wherein said binding molecule is covalently linked to said therapeutically active substance or said diagnostic compound via a linker.

20. The binding molecule of claim 4, wherein said binding molecule binds L1CAM with an affinity (KD) of at least $10^{-10}$ M.

21. The binding molecule of claim 4, wherein said mammalian cell is a SKOV3ip cell.

22. A method for treating a tumor disease in a patient, comprising administering to said patient a therapeutically effective amount of a binding molecule of claim 1.

23. The method of claim 22, wherein the tumor disease is an epithelial tumor disease and/or is selected from the group consisting of astrocytoma, oligodendroglioma, meningioma, neurofibroma, glioblastoma, ependymoma, Schwannoma, neurofibrosarcoma, medulloblastoma, melanoma, pancreatic cancer, prostate carcinoma, head and neck cancer, breast cancer, lung cancer, ovarian cancer, endometrial cancer, renal cancer, neuroblastoma, squamous carcinoma, medulloblastoma, hepatoma, colon cancer, mesothelioma and epidermoid carcinoma.

24. A method for treating a tumor disease in a patient, comprising administering to said patient a therapeutically effective amount of a binding molecule of claim 6.

25. The method of claim 24, wherein the tumor disease is an epithelial tumor disease and/or is selected from the group consisting of astrocytoma, oligodendroglioma, meningioma, neurofibroma, glioblastoma, ependymoma, Schwannoma, neurofibrosarcoma, medulloblastoma, melanoma, pancreatic cancer, prostate carcinoma, head and neck cancer, breast cancer, lung cancer, ovarian cancer, endometrial cancer, renal cancer, neuroblastoma, squamous carcinoma, medulloblastoma, hepatoma, colon cancer, mesothelioma and epidermoid carcinoma.

\* \* \* \* \*

SEQUENCE LISTING

```
<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: light chain VJ domain of L1-OV52.24

<400> SEQUENCE: 1

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly His Ser Pro Lys Ala Leu Ile
        35                  40                  45

Tyr Ser Thr Ser Tyr Arg Tyr Ser Gly Val Pro Asp Arg Phe Thr Gly
    50                  55                  60

Ser Gly Ser Gly Thr Asp Phe Thr Leu Thr Ile Arg Asn Val Gln Ser
65                  70                  75                  80

Glu Asp Leu Ala Glu Tyr Phe Cys Gln Gln Tyr Asn Thr Tyr Pro Tyr
                85                  90                  95

Thr Phe Gly Gly Gly Thr Lys Leu Glu Ile Lys
            100                 105

<210> SEQ ID NO 2
<211> LENGTH: 115
<212> TYPE: PRT
<213> ORGANISM: Artificial Sequence
<220> FEATURE:
<223> OTHER INFORMATION: heavy chain VDJ domain of L1-OV52.24

<400> SEQUENCE: 2

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met Gln Trp Val Lys Gln Arg Pro Glu Gln Gly Leu Glu Trp Ile
        35                  40                  45

Gly Trp Ile Asp Pro Glu Asn Gly Lys Thr Val Phe Asp Pro Lys Phe
    50                  55                  60

Arg Gly Lys Ala Ser Ile Ser Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Trp Asn Pro Leu Ala Phe Trp Gly Gln Gly Thr Leu Val Thr
```

Val Ser Ser
    115

<210> SEQ ID NO 3
<211> LENGTH: 816
<212> TYPE: DNA
<213> ORGANISM: Artificial Sequence
<220> FEATURE:
<223> OTHER INFORMATION: light chain sequence

<400> SEQUENCE: 3

| | | | | | |
|---|---|---|---|---|---|
| tttgatgact | gctttgcata | gatccctaga | ggccagccca | gctgcccatg | atttataaac | 60 |
| caggtctttg | cagtgagatc | tgaaatacat | cagatcagca | tgggcatcaa | gatggagtca | 120 |
| cagactcagg | tctttgtata | catgttgctg | tggttgtctg | gtgttgatgg | agacattgtg | 180 |
| atgacccagt | ctcaaaaatt | catgtccaca | tcagtaggag | acagggtcag | cgtcacctgc | 240 |
| aaggccagtc | agaatgtggg | tactaatgtg | gcctggtatc | aacagaaacc | aggtcactct | 300 |
| cctaaagcac | tgatttactc | gacatcctac | cggtacagtg | gagtccctga | tcgcttcaca | 360 |
| ggcagtggat | ctgggacaga | tttcactctc | accatccgca | atgtgcagtc | tgaagacttg | 420 |
| gcagagtact | tctgtcagca | atataacacc | tatccgtaca | cgttcggagg | ggggaccaag | 480 |
| ctggaaataa | aacgggctga | tgctgcacca | actgtatcca | tcttcccacc | atccagtgag | 540 |
| cagttaacat | ctggaggtgc | ctcagtcgtg | tgcttcttga | caacttcta | ccccaaagac | 600 |
| atcaatgtca | agtggaagat | tgatggcagt | gaacgacaaa | atggcgtcct | gaacagttgg | 660 |
| actgatcagg | acagcaaaga | cagcacctac | agcatgagca | gcaccctcac | gttgaccaag | 720 |
| gacgagtatg | aacgacataa | cagctatacc | tgtgaggcca | ctcacaagac | atcaacttca | 780 |
| cccattgtca | agagcttcaa | caggaatgag | tgttag | | | 816 |

<210> SEQ ID NO 4
<211> LENGTH: 1490
<212> TYPE: DNA
<213> ORGANISM: Artificial Sequence
<220> FEATURE:
<223> OTHER INFORMATION: heavy chain sequence

<400> SEQUENCE: 4

| | | | | | |
|---|---|---|---|---|---|
| ctgcctcatg | aatatgcaaa | catgagtctg | tgattataaa | tacagagata | tccataccaa | 60 |
| acaacttatg | agcactgttt | tctctacagt | cactgaatct | caaggtcctt | acaatgcaat | 120 |
| gcagctgggt | catcttcttc | ctgatggcag | tggttacagg | ggtcaattca | gaggttcagc | 180 |
| tgcagcagtc | tggggctgag | cttgtgaggc | caggggcctt | agtcaagttg | tcctgcaaag | 240 |
| cttctggctt | caacattaaa | gactactata | tgcagtgggt | gaagcagagg | cctgaacagg | 300 |
| gcctggagtg | gattggatgg | attgatcctg | agaatggtaa | acagtttttt | gacccgaagt | 360 |
| tccggggcaa | ggccagtata | tcagcggaca | catcctccaa | cacagcctac | ctgcagctca | 420 |
| gcagcctgac | atctgaggac | actgccgtct | attactgtgc | tagatggaac | cccttgcct | 480 |
| tctggggcca | agggactctg | gtcactgtct | ctgcagccaa | aacgacaccc | ccatctgtct | 540 |
| atccactggc | cctggatct | gctgcccaaa | ctaactccat | ggtgaccctg | ggatgcctgg | 600 |
| tcaagggcta | tttccctgag | ccagtgacag | tgacctggaa | ctctggatcc | ctgtccagcg | 660 |
| gtgtgcacac | cttcccagct | gtcctggagt | ctgacctcta | cactctgagc | agctcagtga | 720 |
| ctgtcccctc | cagccctcgg | cccagcgaga | ccgtcacctg | caacgttgcc | cacccggcca | 780 |

-continued

```
gcagcaccaa ggtggacaag aaaattgtgc ccagggattg tggttgtaag ccttgcatat    840
gtacagtccc agaagtatca tctgtcttca tcttcccccc aaagcccaag gatgtgctca    900
ccattactct gactcctaag gtcacgtgtg ttgtggtaga catcagcaag gatgatcccg    960
aggtccagtt cagctggttt gtagatgatg tggaggtgca cacagctcag acgcaaccc   1020 gggaggagca gttcaacagc actttccgct cagtcagtga acttcccatc atgcaccagg   1080
actggctcaa tggcaaggag ttcaaatgca gggtcaacag tgcagctttc ctgcccccca   1140
tcgagaaaac catctccaaa accaaaggca gaccgaaggc tccacaggtg tacaccattc   1200
cacctcccaa ggagcagatg gccaaggata aagtcagtct gacctgcatg ataacagact   1260
tcttccctga agacattact gtggagtggc agtggaatgg gcagccagcg gagaactaca   1320
agaacactca gcccatcatg aacacgaatg gctcttactt cgtctacagc aagctcaatg   1380
tgcagaagag caactgggag gcaggaaata ctttcacctg ctctgtgtta catgagggcc   1440
tgcacaacca ccatactgag aagagcctct cccactctcc tggtaaatga             1490
```

```
<210> SEQ ID NO 5
<211> LENGTH: 11
<212> TYPE: PRT
<213> ORGANISM: Artificial Sequence
<220> FEATURE:
<223> OTHER INFORMATION: LCDR1

<400> SEQUENCE: 5

Lys Ala Ser Gln Asn Val Gly Thr Asn Val Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: LCDR2

<400> SEQUENCE: 6

Ser Thr Ser Tyr Arg Tyr Ser
1               5

<210> SEQ ID NO 7
<211> LENGTH: 9
<212> TYPE: PRT
<213> ORGANISM: Artificial Sequence
<220> FEATURE:
<223> OTHER INFORMATION: LCDR3

<400> SEQUENCE: 7

Gln Gln Tyr Asn Thr Tyr Pro Tyr Thr
1               5

<210> SEQ ID NO 8
<211> LENGTH: 9
<212> TYPE: PRT
<213> ORGANISM: Artificial Sequence
<220> FEATURE:
<223> OTHER INFORMATION: HCDR1

<400> SEQUENCE: 8

Phe Asn Ile Lys Asp Tyr Tyr Met Gln
1               5

<210> SEQ ID NO 9
<211> LENGTH: 17
```

```
<212> TYPE: PRT
<213> ORGANISM: Artificial Sequence
<220> FEATURE:
<223> OTHER INFORMATION: HCDR2

<400> SEQUENCE: 9

Trp Ile Asp Pro Glu Asn Gly Lys Thr Val Phe Asp Pro Lys Phe Arg
1               5                   10                  15

Gly

<210> SEQ ID NO 10
<211> LENGTH: 6
<212> TYPE: PRT
<213> ORGANISM: Artificial Sequence
<220> FEATURE:
<223> OTHER INFORMATION: HCDR3

<400> SEQUENCE: 10

Trp Asn Pro Leu Ala Phe
1               5
```